United States Patent
Ishii et al.

(10) Patent No.: US 8,409,447 B2
(45) Date of Patent: Apr. 2, 2013

(54) SEPARATION CHIP AND SEPARATION METHOD

(75) Inventors: Kentaro Ishii, Kanagawa (JP); Masashi Higasa, Kanagawa (JP); Shingo Hiramatsu, Kanagawa (JP)

(73) Assignee: Toray Industries, Inc. (JP)

( * ) Notice: Subject to any disclaimer, the term of this patent is extended or adjusted under 35 U.S.C. 154(b) by 391 days.

(21) Appl. No.: 12/864,283

(22) PCT Filed: Jan. 27, 2009

(86) PCT No.: PCT/JP2009/051278
§ 371 (c)(1),
(2), (4) Date: Jul. 23, 2010

(87) PCT Pub. No.: WO2009/096391
PCT Pub. Date: Aug. 6, 2009

(65) Prior Publication Data
US 2010/0294732 A1    Nov. 25, 2010

(30) Foreign Application Priority Data

Jan. 28, 2008   (JP) ................................. 2008-016259

(51) Int. Cl.
*B01D 21/26* (2006.01)
*B04B 5/04* (2006.01)
*G01N 33/49* (2006.01)

(52) U.S. Cl. .......... 210/782; 210/787; 210/206; 422/72; 422/506; 422/533; 435/45; 435/177

(58) Field of Classification Search ................ 210/782, 210/787, 206; 422/72, 506, 533; 436/45, 436/177
See application file for complete search history.

(56) References Cited

U.S. PATENT DOCUMENTS

| 4,557,600 | A | 12/1985 | Klose et al. |
| 4,892,708 | A | 1/1990 | Wogoman |
| 5,089,417 | A | 2/1992 | Wogoman |
| 7,691,328 | B2 * | 4/2010 | Horiike et al. ............... 422/533 |

FOREIGN PATENT DOCUMENTS

| JP | 63-105862 | U | * | 7/1988 |
| JP | 64-025058 | A | | 1/1989 |
| JP | 2004-109082 | | | 4/2004 |
| JP | 2006-200923 | A | | 8/2006 |
| JP | 2007-078676 | A | | 3/2007 |
| JP | 2007-198949 | A | | 8/2007 |
| JP | 2007-232673 | A | | 9/2007 |

OTHER PUBLICATIONS

Partial Translation of JP 63-105862 U (Titled "Japanease Utility Model Publication No. SHO63-105862"), pp. 1-3, Jul. 8, 1988.*
The International Prliminary Report on Patentability for PCT/JP2009/051278, Aug. 31, 2010.*

* cited by examiner

*Primary Examiner* — David A Reifsnyder
(74) *Attorney, Agent, or Firm* — DLA Piper LLP (US)

(57) ABSTRACT

A separation chip for separating an insoluble component from a suspension using centrifugal force by rotation, includes a suspension holding tank, a separation liquid holding tank, and an insoluble component holding tank arranged in order from an inner circumferential side during rotation, wherein the suspension holding tank and the insoluble component holding tank are connected to each other, the insoluble component holding tank and the separation liquid holding tank are connected to each other by a narrow portion, and in the insoluble component holding tank, a connecting portion with the suspension holding tank is positioned further toward an outer circumferential side than the narrow portion.

15 Claims, 18 Drawing Sheets

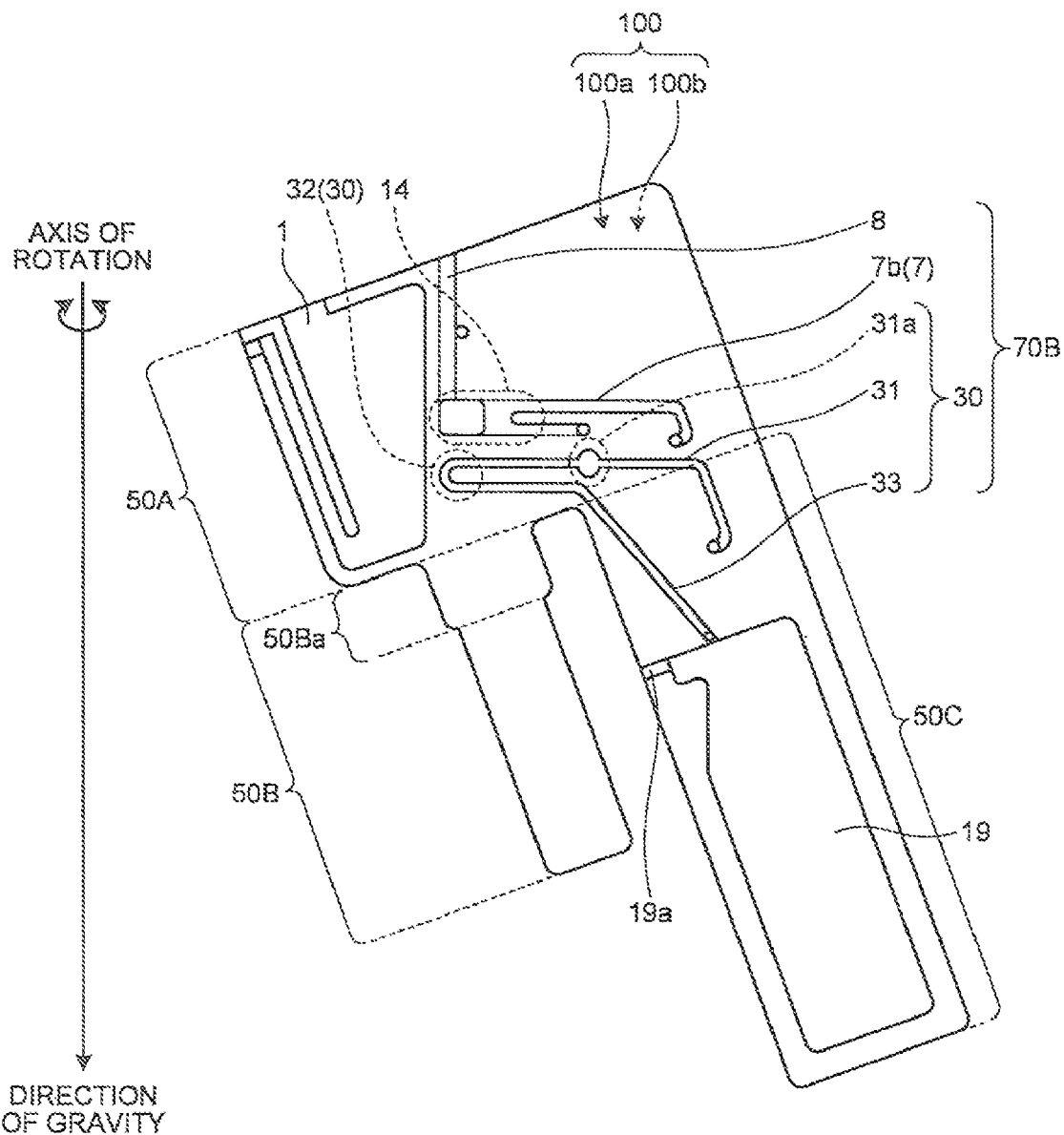

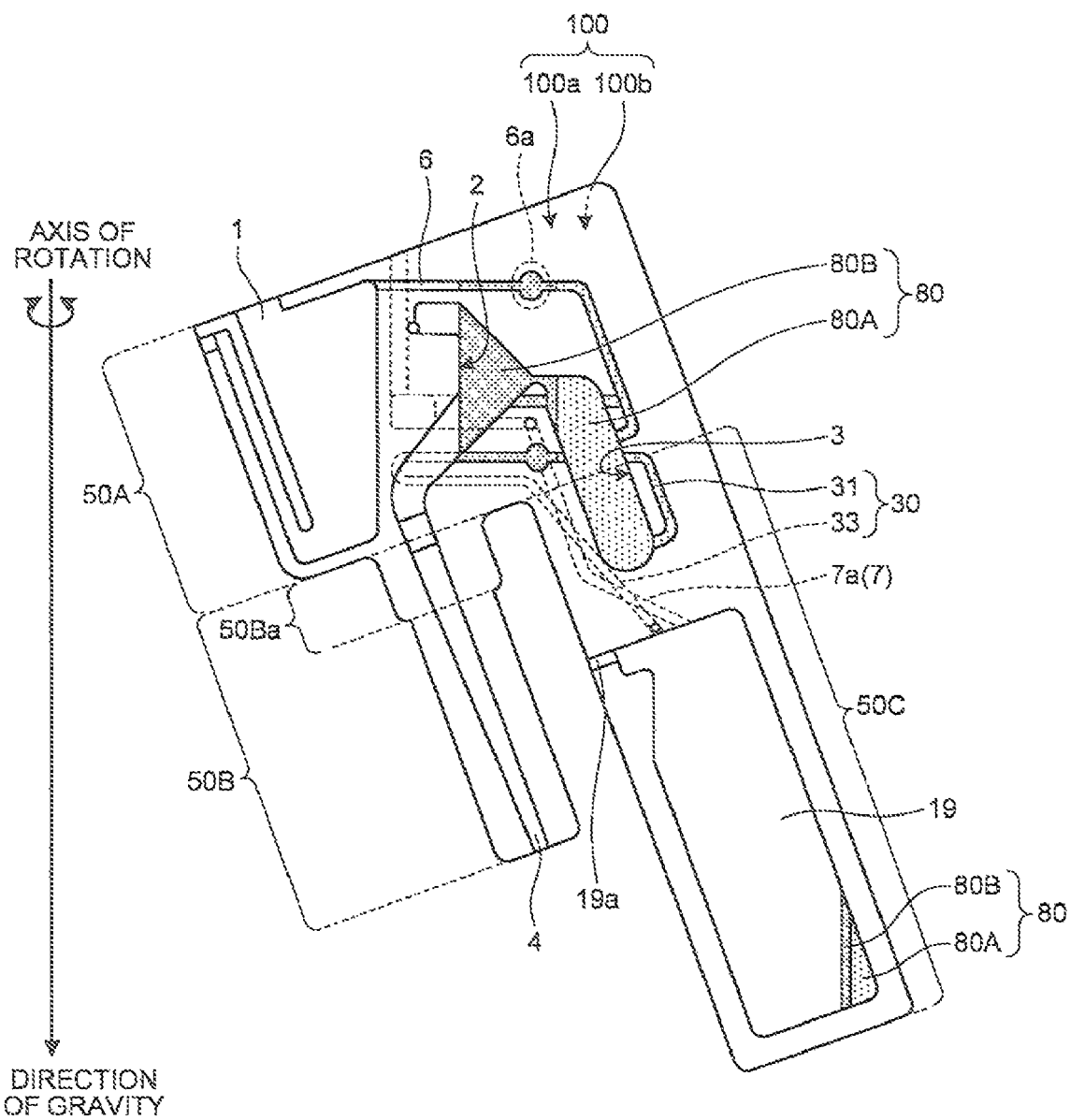

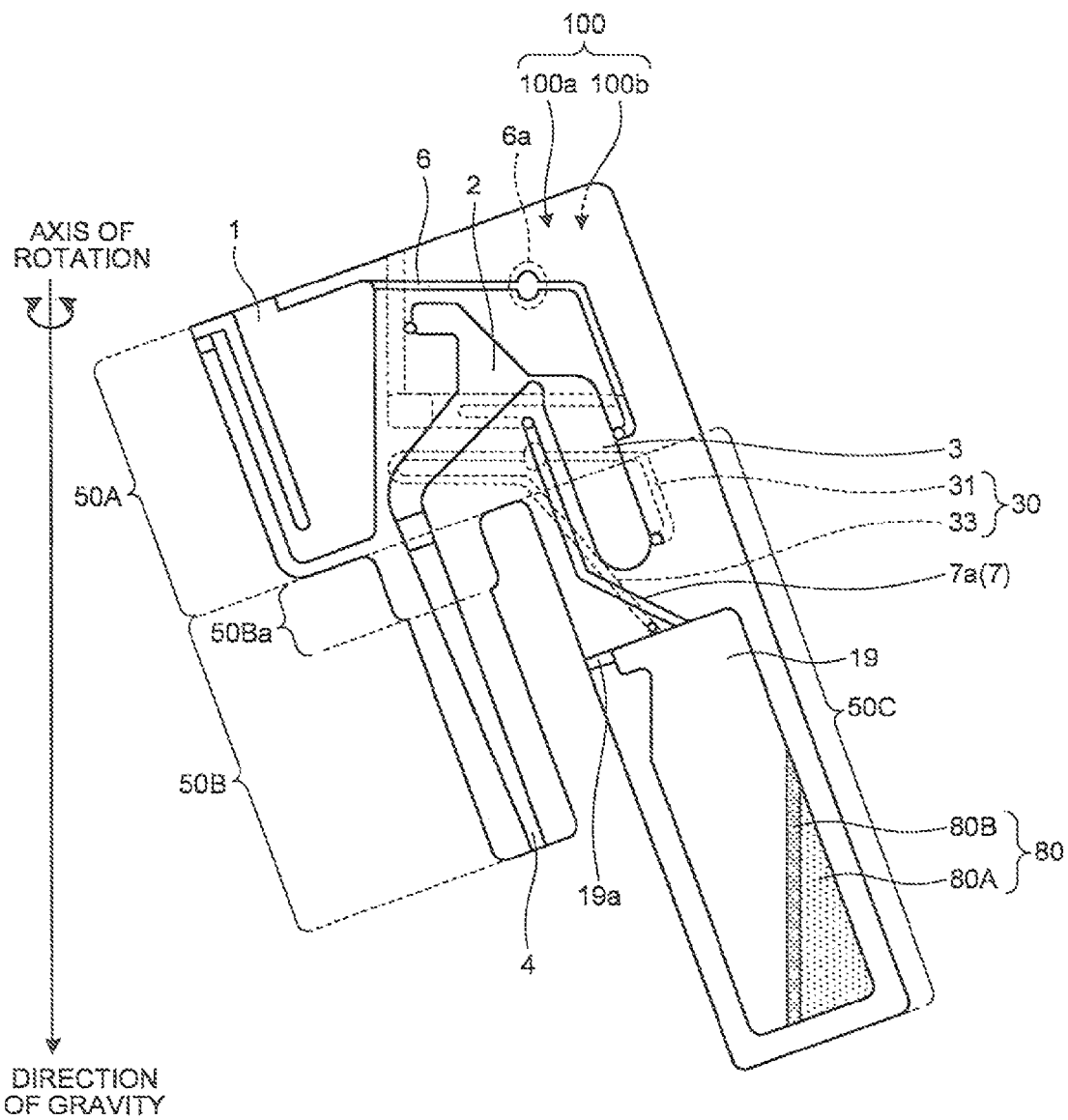

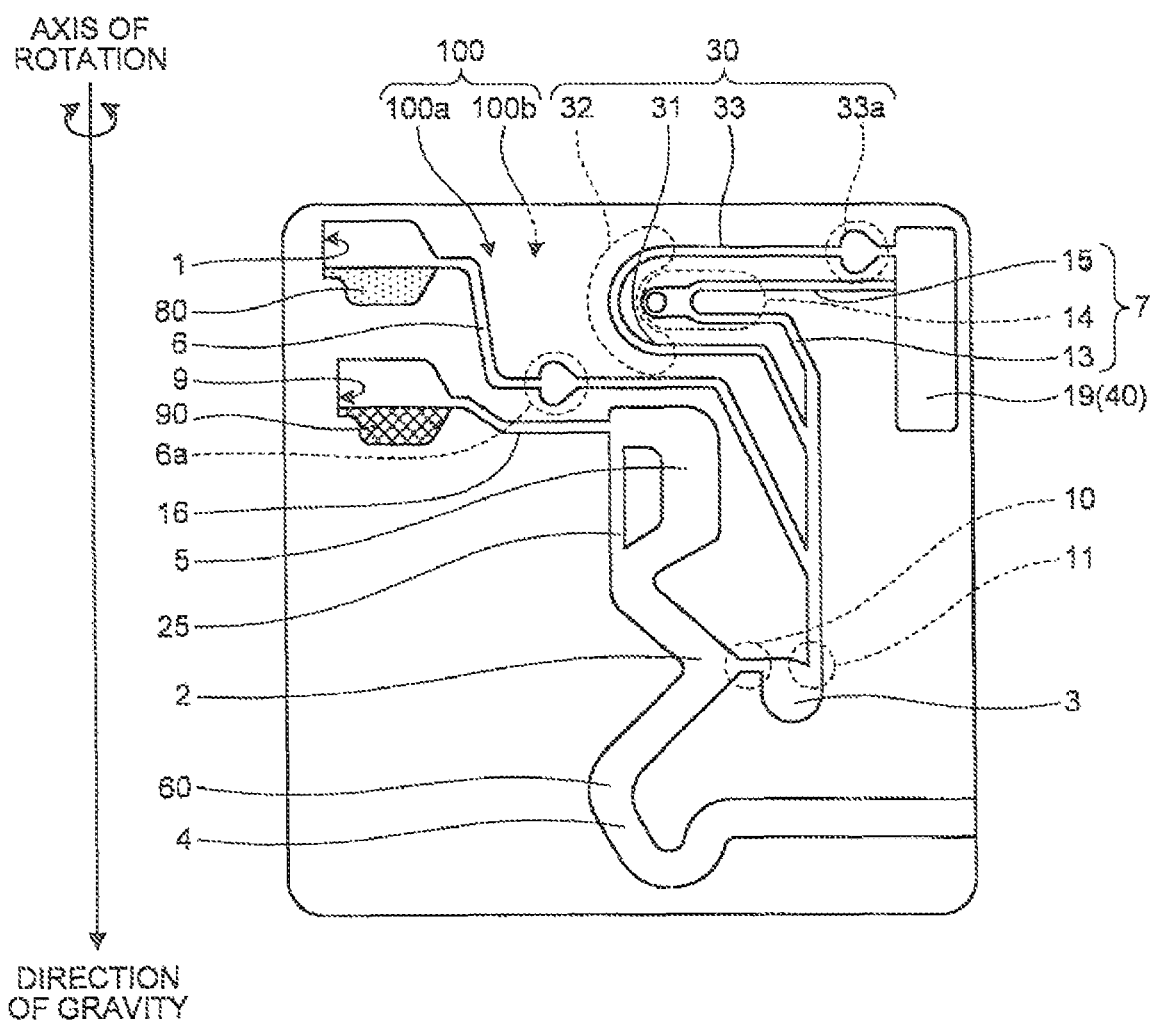

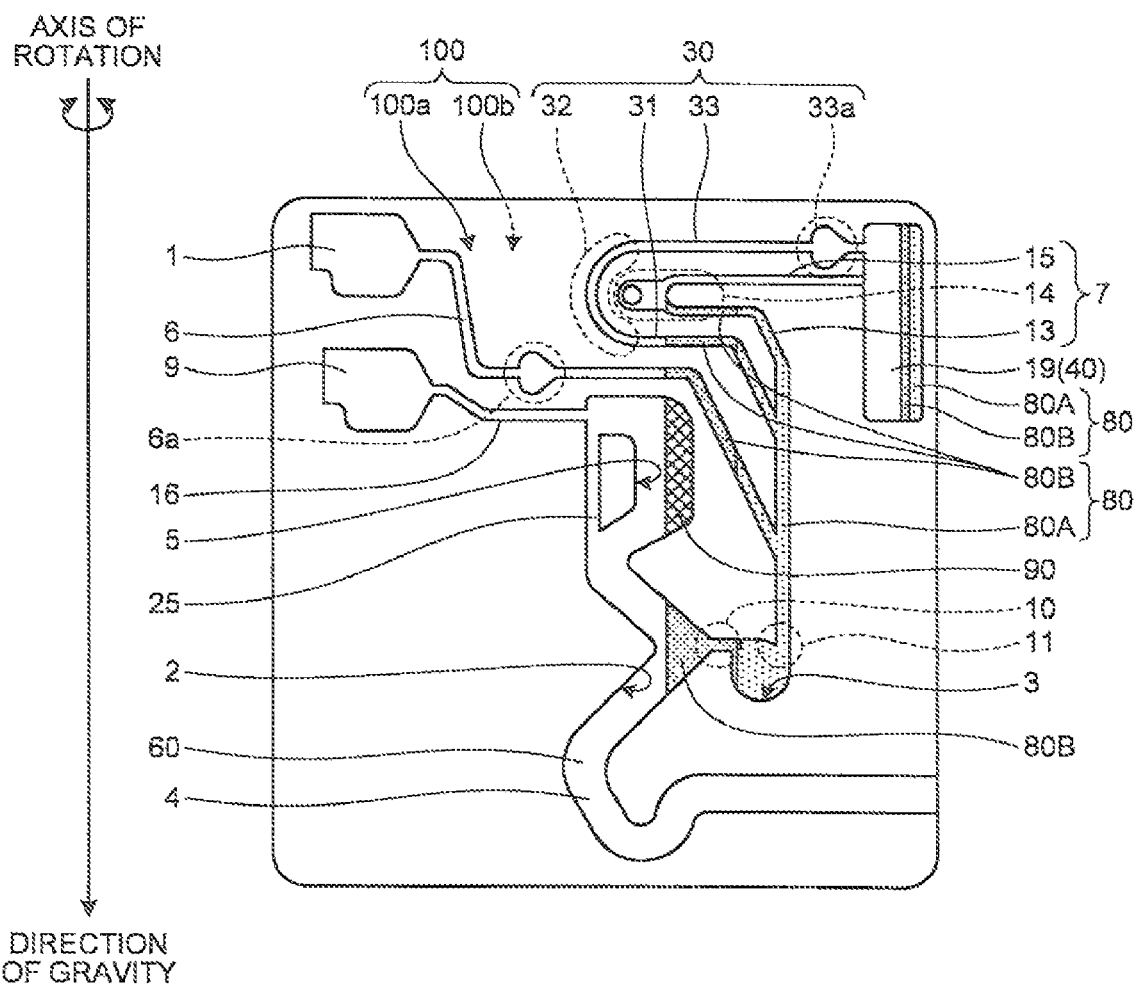

SEPARATION CHIP AND SEPARATION METHOD

RELATED APPLICATIONS

This is a §371 of International Application No. PCT/JP2009/051278, with an international filing date of Jan. 27, 2009 (WO 2009/096391 A1, published Aug. 6, 2009), which is based on Japanese Patent Application No. 2008-016259, filed Jan. 28, 2008, the subject matter of which is incorporated by reference.

TECHNICAL FIELD

This disclosure relates to a separation chip and a separation method. More specifically, the disclosure relates to a separation chip, and a separation method using such separation chip, for separating a suspension such as blood into an insoluble component and a liquid component.

BACKGROUND

Conventionally, most analysis of tiny amount of molecules relating to clinical diagnosis, food hygiene, and environmental analysis has been carried by processing a sample with an apparatus such as a centrifugal separator, a gas chromatography apparatus, and a liquid chromatography apparatus, and then analyzing to a high level of accuracy using a mass spectrometer. These apparatuses are expensive and require specialized knowledge to operate. Therefore, the such separation, measurement, and analysis have been performed by a clinical testing laboratories or an analysis institute. Recently, there is a trend for the need to perform simple and fast diagnosis, analysis and/or measurements at a patient's bedside, and locations where food is processed and imported. More specifically, for example, performing disease diagnosis and analysis of toxic substances in rivers and waste products on site, such as at the patient's bedside, a river, or waste treatment plant, is gaining attention. Consequently, emphasis is being placed on the development of methods and devices capable of separating, measuring, and analyzing a sample simply, rapidly, cheaply, and accurately, yet with a high degree of sensitivity.

In particular, in clinical diagnosis, for early diagnosis of a sickness condition, an important problem to resolve is how to perform detection simply, rapidly, cheaply, and accurately, yet with a high degree of sensitivity, using a small amount of a specimen, while shortening the analysis time and reducing the amount of the specimen (sample) required for the analysis.

Accordingly, recently, to resolve this subject, new devices are being developed which can perform analysis by applying micro fabrication technology. In such devices, fine channels are formed and arranged in a chip several cm in size (square), a very small amount of a specimen (sample) such as blood from a test subject is injected into the chip, and analysis is carried out. Such a device needs functions for collecting blood cells from blood and removing the blood cells, as well as a function for separating a specific component from a small amount of a (living) sample. Various techniques have been developed for such purposes.

For example, a technique is known for separating a specific component by rotating a chip to apply centrifugal force.

JP 3803078 discloses a technique in which blood cells are separated from blood by rotating a chip having fine channels arranged in an approximately horizontal plane, and after stopping rotation, a plasma component is isolated using an external suction pump.

The chip disclosed in JP 3803078 has a structure including (1) a tank for holding blood which includes a blood cell component, (2) a channel which is connected to and positioned further toward the outer circumferential side of the tank holding the blood and which has a function for holding plasma, and (3) a blood cell fraction containing portion which is connected to and positioned on the outer circumferential side of the channel holding plasma.

Furthermore, JP 2006-200923 describes a chemical analysis device capable of isolating serum utilizing centrifugal force, capillarity, and a siphon effect by repeatedly rotating and stopping a chip having fine channels which are arranged in an approximately horizontal plane.

This chip has (1) a tank for holding a suspension such as blood including a blood cell component, (2) a tank for holding a separation liquid such as serum which is further on the outer circumferential side than the tank holding the suspension, and (3) a tank for holding an insoluble component such as blood cells, the tank being connected to the separation liquid holding tank by a narrow portion such as a weir, this tank being further toward the outer circumferential side than the tank holding the separation liquid. In this chip, the tank holding the suspension and the tank holding the separation liquid are connected by a narrow portion such as a weir.

Furthermore, a capillary tube is used for causing capillary flow from the tank holding the separation liquid due to surface tension.

In the chip disclosed in JP 3803078, after blood cell separation, the plasma component is recovered by connecting an external connection suction pump. Therefore, the chip disclosed in JP 3803078 needs an external connection suction pump to be prepared and requires time and efforts for the connection. Thus, this chip cannot be said to be simple, fast, and low-cost analysis means.

The chip disclosed in JP 3803078 has a blood cell fraction containing portion further toward the outer circumferential side than the channel having a function for holding plasma. In this chip, during the isolation and recovery of plasma by a suction pump, the blood cell component needs to adhere to the blood cell fraction containing portion. However, clinical blood specimens exhibit a varied nature in which blood cell characteristics such as viscosity, composition, and hemolysis differ according to individual differences, clinical condition and the like. Therefore, for such a clinical blood specimen, because the adherence of the blood cell component at the blood cell fraction containing portion may be insufficient, the blood cell component may be mixed with and enter the plasma due to the suction force which is applied on the blood cell fraction containing portion during suction recovery with the pump. Thus, to prevent the risk of the blood cell component mixed with and entering the plasma by reducing the suction force applied on the blood cell fraction during suction recovery with a pump, JP 3803078 discloses a technique which employs a narrow structure as the connecting portion of the channel having a function for holding plasma with the blood cell fraction containing portion.

However, since the connecting portion with the channel having a function for holding plasma is a narrow structure, the blood cell fraction containing portion suffers from the problem that the connecting portion tends to become blocked by the blood cell component. Furthermore, since the blood cell fraction containing portion is a sealed space other than the connecting portion with the channel having a function for holding plasma, there is no place for gases to escape. Therefore, for clinical blood specimens having a varied nature in which viscosity, composition and the like differ according to individual differences, clinical condition and the like, a gas layer forms in the blood cell fraction containing portion, which may prevent blood from entering and cause gas bubbles to remain in the blood cell fraction containing portion.

The chip disclosed in JP 2006-200923 does not require an external connection pump, but rather leads serum to a downstream mixing portion due to capillary flow by stopping the chip after a serum separation operation. However, in the chip disclosed in JP 2006-200923, the channel and various tanks are arranged so that the suspension passes through a separation liquid holding tank due to centrifugal force by rotation, then flows through a narrow portion and into an insoluble component holding tank.

More specifically, since the insoluble component holding tank is a sealed space other than a suspension flow inlet, there is no place for gases to escape. Therefore, for clinical blood specimens having a varied nature in which viscosity, composition and the like differ according to individual differences, clinical condition and the like, a gas layer forms in the insoluble component holding tank. This gas layer may prevent the suspension from entering, cause gas bubbles to remain in the insoluble component holding tank, and cause the insoluble component to remain in the separation liquid holding tank. If gas bubbles remain in the insoluble component holding tank, the quantitative performance of the separation liquid may be harmed. In such a case, although providing a vent hole in the insoluble component holding tank improves on this problem, it is impossible to completely prevent gas bubbles from remaining.

Furthermore, the chip disclosed in JP 2006-200923 recovers and isolates serum by a siphon effect produced by causing a separation liquid separated by rotation to capillary flow in a serum capillary tube serving as a separation liquid discharge channel due to surface tension after rotation is stopped, and then again rotating. Thus, it is necessary to cause capillary flow just by surface tension in a fine channel in a state where there is no action of centrifugal force. However, as described above, it is difficult to produce a constantly stable capillary flow for clinical blood specimens such as serum having a varied nature in which viscosity, composition and the like differ according to individual differences, clinical condition and the like. To produce a stable capillary flow, the diameter of the tube needs to be as small as possible. However, decreasing the diameter of the tube increases the risk of the siphon effect easily failing to work due to the entry of solid matter such as blood clots into the serum capillary tube, and the occurrence and entry of gas bubbles inside the capillary tube.

Thus, if a separation liquid such as serum cannot be stably recovered and isolated in a correct amount, an error or a mistake may be produced in the obtained analysis and test result. Especially in the medical field, this is a serious problem.

Moreover, the chip disclosed in JP 2006-200923 has to be rotated, stopped, and again rotated to recover and isolate the serum.

Further, in the case of providing a folded back portion in an overflow channel to increase the quantitative performance, when suspension which has passed the folded back portion during rotation flows toward an overflow liquid holding tank, the suspension which should flow into the insoluble component holding tank may flow back toward the folded back portion due to siphoning. More specifically, pre-separation suspension may flow out due to the occurrence of siphoning caused by suspension which has filled the overflow channel during rotation. Consequently, the quantitative performance may be harmed.

In view of such a situation, it could be helpful to provide a separation chip capable of stably separating an insoluble component and a liquid component in a suspension more accurately without requiring an external device such as an external connection pump. Furthermore, it could also be helpful to provide a method for separating a desired component using this separation chip.

SUMMARY

We discovered that, in a separation chip for removing an insoluble component from a suspension using a centrifugal force by rotation, the above-described problems can be resolved by a structure using a narrow structure as a connecting portion between a separation liquid holding tank and an insoluble component holding tank, and connecting a suspension holding tank and the insoluble component holding tank, so as to have a mechanism in which, first, the suspension is introduced due to centrifugal force into the insoluble component holding tank which is positioned on the outer circumferential side of the narrow connecting portion, and a separated separation liquid (liquid component) fills the separation liquid holding tank positioned further toward the inner circumferential side via the narrow portion during rotation.

We thus provide:
(1) A separation chip for separating an insoluble component from a suspension using centrifugal force by rotation, comprising:
  a suspension holding tank, a separation liquid holding tank, and an insoluble component holding tank which are arranged in this order from an inner circumferential side during rotation,
  wherein the suspension holding tank and the insoluble component holding tank are connected with each other,
  the insoluble component holding tank and the separation liquid holding tank are connected with each other by a narrow portion, and
  in the insoluble component holding tank, a connecting portion with the suspension holding tank is positioned further toward an outer circumferential side than the narrow portion.
(2) The separation chip according to above the (1), wherein the suspension holding tank and the insoluble component holding tank are connected with each other by a suspension introduction channel, and an opening of the suspension introduction channel in the insoluble component holding tank is positioned further toward an outer circumferential side than the narrow portion, and
  the separation liquid holding tank is a tank which can hold a liquid component which has passed through the narrow portion.
(3) The separation chip according to above the (1), wherein the connecting portion between the insoluble component holding tank and the suspension holding tank is positioned on a wall face of the insoluble component holding tank on the outer circumferential side.
(4) The separation chip according to any one of above the (1) to (3), further comprising a separation liquid discharge channel which is connected to the separation liquid holding tank, extends in the direction of gravity, and discharges the liquid component from the separation liquid holding tank.

(5) The separation chip according to above the (4), wherein the separation liquid discharge channel extends toward the outer circumferential side and the direction of gravity.

(6) The separation chip according to above the (4) or (5), wherein the separation liquid discharge channel has a section midway along the channel having a smaller channel cross-sectional area than a channel cross-sectional area at a connecting portion with the separation liquid holding tank.

(7) The separation chip according to any one of above the (1) to (6), wherein the narrow portion is positioned above the insoluble component holding tank.

(8) The separation chip according to any one of above the (1) to (7), further comprising a washing solution holding tank which is positioned above the separation liquid holding tank, is connected to the separation liquid holding tank, and can hold a washing solution during rotation.

(9) The separation chip according to any one of above the (1) to (8), further comprising an overflow channel which has one end connected to the suspension introduction channel and the insoluble component holding tank, and wherein the overflow channel first extends toward the inner circumferential side from a connecting portion with the suspension introduction channel or the insoluble component holding tank, then changes direction and extends toward the outer circumferential side.

(10) The separation chip according to above the (9), wherein the folded back portion of the overflow channel further comprises a vent hole in communication with outside of the separation chip.

(11) The separation chip according to any one of the above (1) to (10), further comprising an insoluble component discharge channel which is connected to one or two or more selected from the group consisting of the insoluble component holding tank, the suspension introduction channel, and the overflow channel.

(12) The separation chip according to above the (11), wherein the insoluble component discharge channel first extends toward the inner circumferential side from a connecting portion with the insoluble component holding tank, and then folds back toward the outer circumferential side at the inner circumferential side further than the folded back portion of the overflow channel.

(13) The separation chip according to above the (12), wherein the folded back portion of the insoluble component discharge channel is positioned above the narrow portion.

(14) A method for separating an insoluble component from a suspension using the separation chip according to any one of above the (1) to (13), comprising:
 separating and holding the insoluble component using centrifugal force by rotating the separation chip, in which a suspension is introduced into the suspension holding tank, around an axis of rotation to feed the suspension to the insoluble component holding tank;
 holding in the separation liquid holding tank the liquid component which is separated by the centrifugal force and which passes through the narrow portion connecting the insoluble component holding tank and the separation liquid holding tank; and
 discharging the liquid component held in the separation liquid holding tank from the separation liquid holding tank by stopping rotation of the separation chip.

(15) The separation method according to above the (14), wherein the suspension is blood.

According to the separation chip, an insoluble component and a liquid component in a suspension can be more accurately and stably separated.

Furthermore, according to the separation chip, by enabling a liquid to be fed by gravity, when rotation is stopped, a separation liquid can be recovered and isolated more stably and more reliably than by capillarity flow due to surface tension.

In addition, according to the separation chip, by providing a separation liquid discharge channel extending in the direction of gravity from a separation liquid holding tank, a separation liquid which has filled the separation liquid holding tank during rotation can be fed to another tank by the action of gravity just by stopping rotation, thereby enabling the separation liquid to be recovered or moved to the next analysis stage.

Still further, according to the separation chip, by providing a washing solution holding tank for holding a washing solution during rotation above the separation liquid holding tank, a washing solution can be fed using the action of gravity, which enables the separation liquid holding tank and channels to be cleaned. Therefore, the separation liquid recovery ratio and quantitative performance can be improved without increasing the number of steps.

Moreover, according to the separation chip, by providing a vent hole on an inner circumferential side of a folded back portion, the occurrence of siphoning can be prevented. Siphoning causes the pre-separated suspension to flow out, thereby harming the quantitative performance. Thus, by preventing a siphoning from occurring, this problem can be resolved.

Furthermore, according to the separation chip, providing an insoluble component discharge channel can prevent the problem of, after a liquid component separated by gravity is discharged from the chip, a part of the insoluble component in the insoluble component holding tank and the liquid component leaking into the separation liquid discharge channel when a centrifugal separation step is again performed, which harms the quantitative performance of the isolated liquid component. In addition, the mixing and entering of the insoluble component with the isolated liquid component can also be prevented.

BRIEF DESCRIPTION OF THE DRAWINGS

FIG. 1-2 is a diagram as viewed from a thickness direction schematically illustrating the conventional separation chip illustrated in FIG. 1-1.

FIG. 2 is a plan view schematically illustrating the separation chip of Comparative Example 2.

FIG. 3-1 is a perspective view schematically illustrating an example of a separation chip.

FIG. 3-2 is a diagram as viewed from a thickness direction schematically illustrating the separation chip illustrated in FIG. 3-1.

FIG. 6-1 is a plan view (1) transparently illustrating another configuration example of a separation chip.

FIG. 6-2 is a plan view (2) transparently illustrating another configuration example of a separation chip following on from FIG. 6-1.

FIG. 6-3 is a plan view (3) transparently illustrating another configuration example of a separation chip following on from FIG. 6-2.

FIG. 6-4 is a plan view (4) transparently illustrating another configuration example of a separation chip following on from FIG. 6-3.

FIG. 7-1 is a schematic view (1) illustrating the operation of a separation chip.

FIG. 7-2 is a schematic view (2) illustrating the operation of a separation chip.

FIG. 7-3 is a schematic view (3) illustrating the operation of a separation chip.

FIG. 7-4 is a schematic view (4) illustrating the operation of a separation chip.

FIG. 9-1 is a schematic view (1) illustrating the operation of a separation chip.

FIG. 9-2 is a schematic view (2) illustrating the operation of a separation chip.

FIG. 9-3 is a schematic view (3) illustrating the operation of a separation chip.

FIG. 9-4 is a schematic view (4) illustrating the operation of a separation chip.

Figure 1:
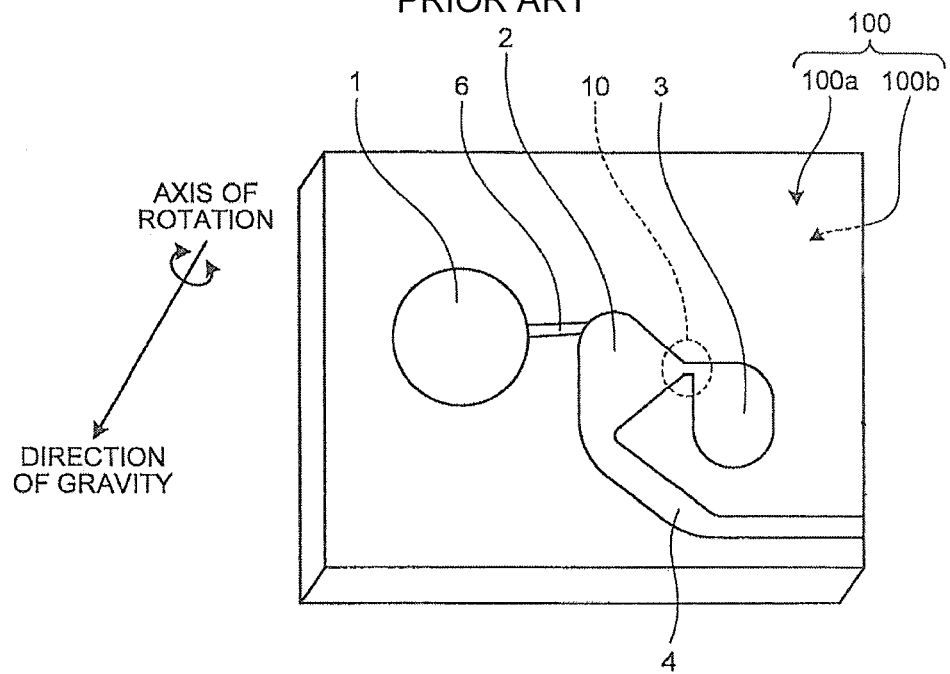
FIG. 1-1 is a perspective view schematically illustrating a configuration example of a conventional separation chip.

| Explanations of Letters or Numerals | |
|---|---|
| 1 | suspension holding tank |
| 2 | separation liquid holding tank |
| 3 | insoluble component holding tank |
| 4 | separation liquid discharge channel |
| 4A | first portion area |
| 4B | second portion area |
| 4C | third portion area |
| 5 | washing solution holding tank |
| 6 | suspension introduction channel |
| 6a, 30a, 31a, 33a | stop valve |
| 7, 18 | overflow channel |
| 7a | first overflow channel portion |
| 7b | second overflow channel portion |
| 8, 17, 19a, 20, 22, 23 | vent hole |
| 9 | washing solution storage tank |
| 10 | narrow portion |
| 11, 12 | connecting portion |
| 13, 31 | first half portion |
| 14, 21, 32 | folded back portion |
| 15, 33 | latter half portion |
| 16 | washing solution introduction channel |
| 19, 24 | overflow holding tank |
| 25 | gas channel |
| 30 | insoluble component discharge channel |
| 40 | waste tank |
| 50A | base portion |
| 50B | first protrusion |
| 50Ba | portion area |
| 50C | second protrusion |
| 60 | inflected portion |
| 70A | first channel group |
| 70B | second channel group |
| 80 | suspension |
| 80A | insoluble component |
| 80B | liquid component |
| 90 | washing solution |
| 100 | main surface |
| 100a | first main surface |
| 100b | second main surface |
| 200 | mixture |
| 300 | separation liquid recovery container |

DETAILED DESCRIPTION

Our chips and methods will now be described with reference to the drawings. However, the drawings merely schematically illustrate the shape, size, and arrangement of the constituent elements to the extent where the disclosure can be understood. Our chips and methods are not limited to the following description. The respective constituent elements may be appropriately modified within the scope of the disclosure. Further, in the drawings, patterned portions represent the suspension, the insoluble component, and the liquid component themselves, or portions where these are present. In the drawings used in the following description, identical constituent elements are represented by the same reference numeral. Further, duplicate descriptions may also be omitted.

The separation chip is a chip for separating an insoluble component and a liquid component from a suspension by rotation.

The term "rotation" means to revolve around a circumference with respect to a given center axis (axis of rotation). Here, "rotation" may also be referred to as "revolve," as distinguished from "spin."

The configuration and the operation of the separation chip will now be described with reference to FIGS. 3-1 to 5.

Figures 1, 2:
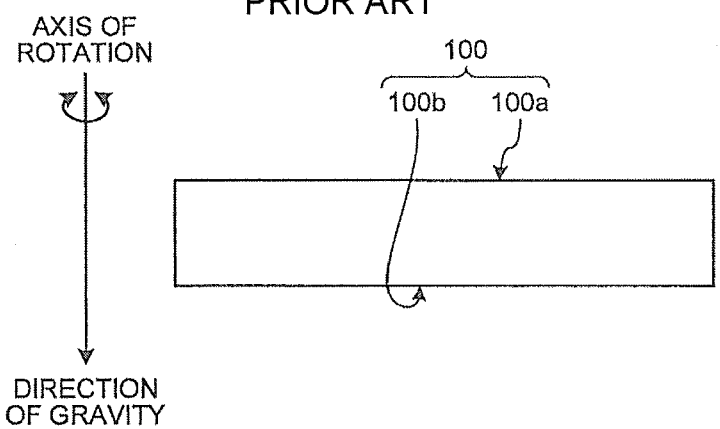
Figure 2:
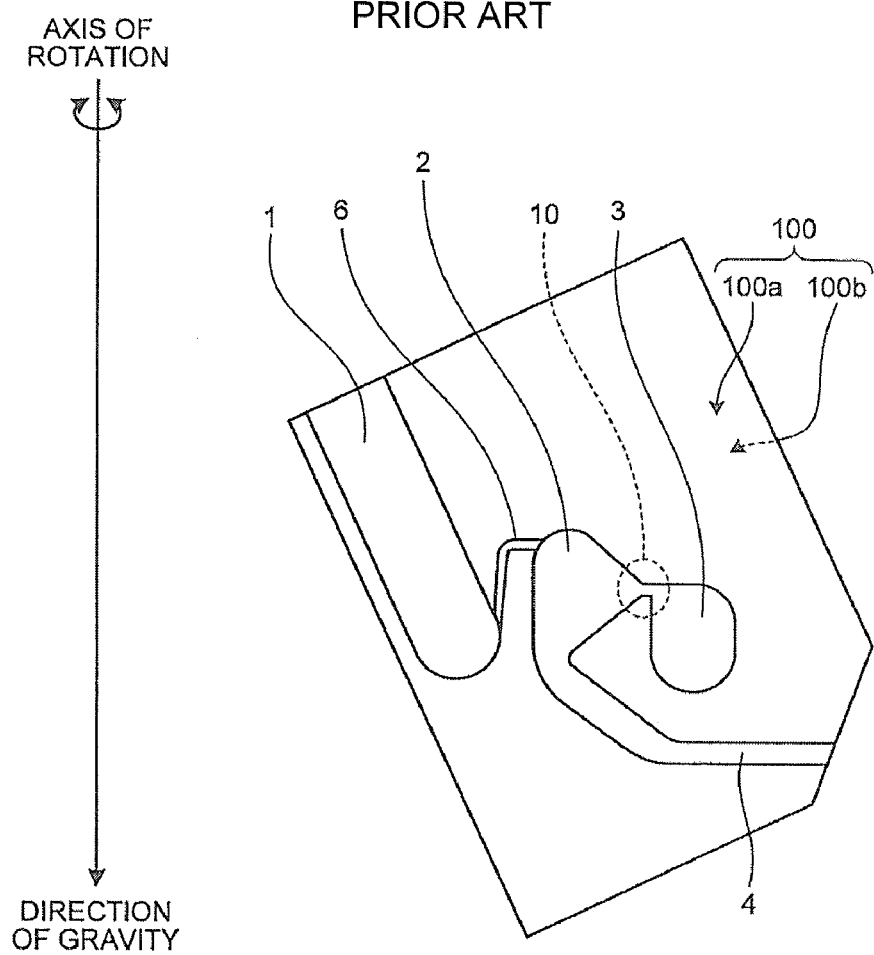
Figures 1, 3:
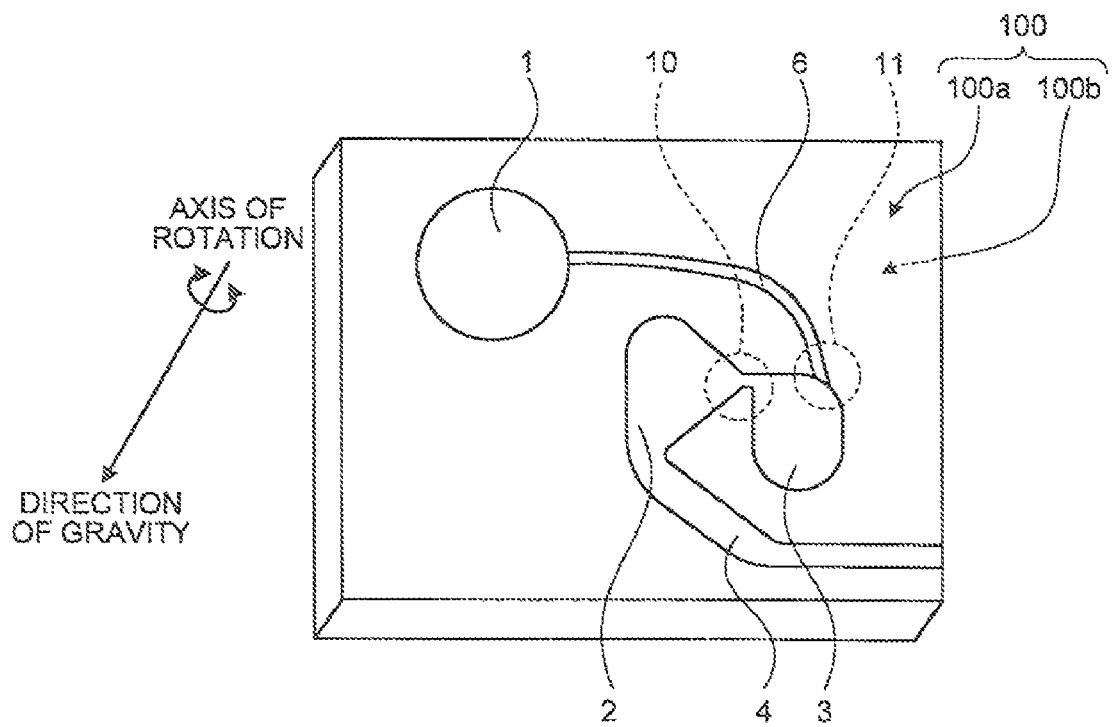
Figures 2, 3:
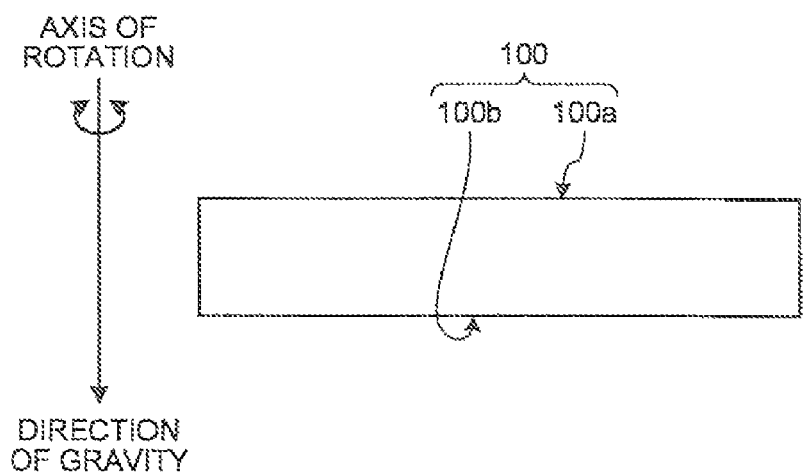
Figure 4:
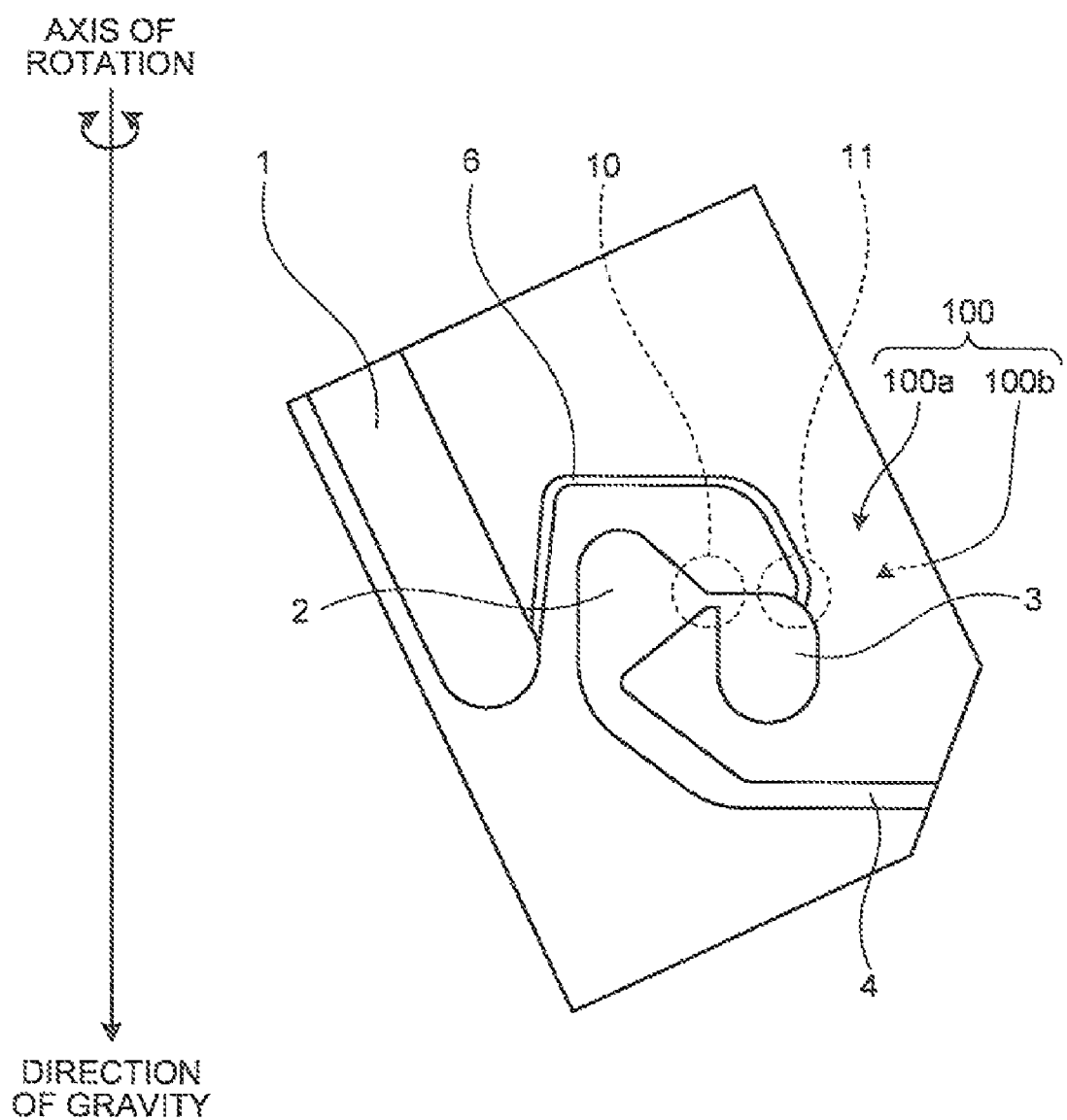
FIG. 4 is a plan view schematically illustrating another configuration example of a separation chip.

FIG. 3-1 is a perspective view schematically illustrating an example of a separation chip. FIG. 3-2 is a diagram as viewed from a thickness direction schematically illustrating the conventional separation chip illustrated in FIG. 3-1. FIG. 4 is a plan view schematically illustrating another example of the separation chip. FIG. 5 is a plan view schematically illustrating another example of the separation chip.

For example, as illustrated in FIGS. 3-1 and 3-2, the separation chip usually has a thin plate-like cuboid or rectangular shape. The separation chip may have a size which allows it to be mounted on a rotation apparatus (centrifuge).

The separation chip has main surfaces 100 which, when viewed transparently, are surfaces on the sides from which the tanks and channels provided as spaces in the solid thickness of the separation chip may be observed. The main surface 100 has, for example, a first main surface 100a and a second main surface 100b facing the first main surface 100a. In each of the drawings, the contours of the tanks and channels in the thickness of the separation chip are depicted by a solid line in principle.

It is preferred to use the separation chip mounted on a rotor. As the rotor, it is more preferred to use an angle rotor. For example, a cylindrical rotor having a thickness of about several centimeters may be used.

Assuming that the separation chip is used by mounting onto an angle rotor, the extension direction (extension angle) of the channels, the shape of the tanks and such features are designed by considering the incline of the chip when it is mounted on the angle rotor.

In the following description, if the separation chip is mounted on a rotation apparatus, specifically, if the separation chip is used on an angle rotor, the shape and the state of the separation chip, and especially the angle, may be described based on the assumption that the separation chip is mounted on an angle rotor and is in an inclined state.

In the following, the description relating to the arrangement relationship using terms such as "above," "below" (direction of gravity), outer circumferential side, inner circumferential side and the like is based on the assumption that the separation chip is in use, specifically, that the separation chip has been placed in a rotation apparatus. As described below, when the separation chip is inclined during rotation, the inclined state serves as a reference. Further, when the separation chip is rotated with the main surfaces 100 being held horizontally, this state serves as a reference for description.

In the following description, the term "outer circumferential side" means the direction in which centrifugal force acts with respect to the axis of rotation, specifically, the direction moving further away from the axis of rotation. The term "inner circumferential side" means the opposite direction from the outer circumferential side, specifically, the direction moving towards the axis of rotation.

Further, the term "direction of gravity" is defined as the direction in which gravity acts during rotation of the separation chip. The term "direction of gravity" may also be expressed as "below" or "downwards." The term "direction of gravity" is not limited to the perpendicular direction, but also includes a direction (approximately perpendicular direction) in which a vector has a perpendicular direction component. Further, the direction of gravity may also mean the direction in which a liquid inside the separation chip flows due to the action of gravity. The term "above" (or "upwards") is defined as the opposite direction to the direction of gravity. In the following description, the terms "above" and "below" may be used to indicate a relative position with respect to a given point of reference.

In addition, in the following description, the term "feed" means causing a liquid (suspension, separation liquid, and washing solution) to fluidly move between a plurality of tanks in the separation chip by, for example, a channel.

The orbit of rotation of the separation chip may be approximately circular. The orbital radius is not especially limited. The direction of the chip during rotation, specifically, the arrangement state, is not especially limited. Generally, the separation chip is rotated so that either of its main surfaces 100 faces upwards or in a rotational circumferential direction.

For example, as illustrated in FIGS. 3-1 and 3-2, when the separation chip is rotated with its main surfaces 100, specifically, the first main surface 100a, facing upwards, the separation chip may be rotated so that the main surfaces 100 (in this example, both the first main surface 100a and the second main surface 100b) are arranged orthogonally, specifically, so that the main surfaces of the separation chip are arranged horizontally, to the axis of rotation extending in the perpendicular direction (direction of gravity).

When the separation chip is rotated with the main surfaces 100 facing the circumferential direction of the orbit of rotation, the separation chip may be rotated with the main surfaces 100 aligned in parallel to the axis of rotation. In this case, the upper corner portion of the separation chip near the axis of rotation may be rotated while inclined toward the axis of rotation side about the lower corner portion thereof near the axis of rotation. More specifically, the separation chip may be rotated so that an edge facing the axis of rotation is inclined so as to form an angle of 10° to 80°, and preferably 20° to 50°, with respect to the axis of rotation.

In the following description, the expression "rotation is stopped" means a state in which rotation is completely stopped and the centrifugal force applied on the separation chip is 0 G. However, even if the rotation is at a very slow speed, such a state is defined as (a state in which) rotation is stopped, as long as the speed is low enough that gravity acts as the motive source of liquid feeding. More specifically, if the centrifugal force applied on the separation chip is about 3 G or less, liquid can be fed in the direction of gravity due to the action of gravity via channels and connecting portions extending in the direction of gravity. Therefore, such a case is included in the expression (a state in which) "rotation is stopped."

The term "suspension" means a liquid in which one or two kinds or more of solids and liquids are mixed. Among such mixtures, a mixture of biological components (a biosample) is preferred. Examples thereof include biosamples such as liquids collected from a living body, such as blood, urine, spinal liquid, saliva, phlegm, and cell suspensions, and cell culture media. Especially, blood and urine are preferred as the suspension used in the separation chip.

The term "insoluble component" means a component separated from a solute (liquid component: separation liquid) by the application of centrifugal force and gravity on the suspension. The insoluble component generally has a greater specific gravity than the separation liquid.

Examples of the insoluble component include cells such as blood cells, a grout-like solid or aggregate of, for example, a blood clot, microbes, and denatured proteins, and crystals of uric acid and the like.

If the suspension is blood, for example, specific examples of the insoluble component to be separated or removed include a cell component, such as a blood cell, and a blood clot. As the separation liquid to be isolated, examples include serum and plasma.

If the suspension is urine, for example, specific examples of the insoluble component to be separated include a cell component and uric acid. As the separation liquid to be isolated, examples include urine supernatant.

As illustrated in FIG. 3-1, for example, the separation chip includes a suspension holding tank 1, a separation liquid holding tank 2, and an insoluble component holding tank 3. These tanks are arranged in the order of suspension holding tank 1, separation liquid holding tank 2, and insoluble component holding tank 3 from the inner circumferential side (side closer to the axis of rotation) when the separation chip is rotated, specifically, in a state in which the separation chip is set on a rotation apparatus.

The suspension holding tank 1 is a tank capable of holding a suspension. The suspension is generally pre-stored in the suspension holding tank 1 before rotation is started (when rotation is stopped) via, in this example, a not-illustrated channel, opening, or vent hole.

The separation liquid holding tank 2 is a tank capable of holding a separation liquid, which is the separated liquid component of the suspension fed from the suspension holding tank 1 when the chip is rotated. The shape of the separation liquid holding tank does not have to be a tank structure, as long as it may temporarily hold the separation liquid when the chip is rotated. Part of a channel wall face (for example, a depressed portion of a curved portion of a channel and the like) may also serve as the separation liquid holding tank.

The insoluble component holding tank 3 is a tank capable of holding an insoluble component which has been separated from the suspension fed from the suspension holding tank 1 when the chip is rotated.

The size of the suspension holding tank 1, the separation liquid holding tank 2, and the insoluble component holding tank 3 may be a capacity which is sufficient to hold the suspension, separation liquid, and insoluble component, respectively. Preferably, the suspension holding tank 1 has a capacity of 10 microliters (μL) to 6000 microliters, the separation liquid holding tank 2 has a capacity of 3 microliters to 4000 microliters, and the insoluble component holding tank 3 has a capacity of 3 microliters to 4000 microliters.

Using an example in which the suspension is blood, it is preferred that the suspension holding tank 1 has a size capable of storing 10 microliters to 6000 microliters of blood. Further, it is preferred that the separation liquid holding tank 2 has a size capable of storing, during rotation, 3 microliters to 2000 microliters of a component other than blood cells, such as plasma. In addition, it is preferred that the insoluble component holding tank 3 has a size capable of holding, during rotation, 7 microliters to 4000 microliters of a component containing blood cells.

In the case of blood, the ratio of the blood cell component, which is the insoluble component, in the blood is generally from 40 to 60%. Therefore, to prevent the blood component from entering the separation liquid holding tank 2, it is preferred to configure so that the ratio between the capacity of the separation liquid holding tank 2 and the capacity of the insoluble component holding tank 3 is greater than 4:6 so that the insoluble component holding tank 3 capacity is larger, and more preferably greater than 3:7.

If the suspension is urine, for example, it is preferred that the suspension holding tank 1 has a size capable of storing 10 microliters to 6000 microliters of urine. Further, it is preferred that the separation liquid holding tank 2 has a size capable of storing, during rotation, 7 microliters to 4000 microliters of urine supernatant. In addition, it is preferred that the insoluble component holding tank has a size capable of holding, during rotation, 3 microliters to 2000 microliters of a component containing uric acid crystals, cells and the like.

In the separation chip, the suspension holding tank 1, the separation liquid holding tank 2, and the insoluble component holding tank 3 are arranged from the axis of rotation side (inner circumferential side) in parallel in that order in the direction (outer circumferential side) becoming more distant from the axis of rotation. The insoluble component holding tank 3 and the separation liquid holding tank 2 are connected by a narrow portion 10 which is more constricted (has a narrower diameter) than these tanks. Therefore, it is preferred that the separation liquid holding tank 2 and the insoluble component holding tank 3 are adjacent to each other. Further, it is preferred that the insoluble component holding tank 3 is positioned further toward the outer circumferential side than the separation liquid holding tank 2. In addition, it is preferred that the suspension holding tank 1 is positioned further toward the inner circumferential side than the separation liquid holding tank 2.

More specifically, the suspension holding tank 1, the separation liquid holding tank 2, and the insoluble component holding tank 3 are arranged in that order in terms of being closer to the axis of rotation. The separation liquid holding tank 2 and the insoluble component holding tank 3 are adjacent to each other, and are connected (in communication with each other) by the narrow portion 10. The suspension holding tank 1 is positioned above and to the inner circumferential side of the insoluble component holding tank 3.

In the separation chip, the suspension holding tank 1 and the insoluble component holding tank 3 are connected by a suspension introduction channel 6, which is a tunnel shaped (worm-eaten hole shape) bore (channel) extending in three dimensions. More specifically, these two tanks are connected without going via the separation liquid holding tank 2. Consequently, compared with a conventional separation chip like that illustrated in FIGS. 1-1 and 1-2, in which a suspension holding tank 1 is in communication with the insoluble component holding tank 3 via the separation liquid holding tank 2, the suspension does not flow into the narrow portion 10 between the separation liquid holding tank 2 and the insoluble component holding tank 3 due to centrifugal force. Further, such a configuration also avoids the problems of blockages and of gas bubbles entering the insoluble component holding tank.

Problems with the conventional chip will now be described with reference to FIGS. 1-1, 1-2, and 2. FIG. 1-1 is a perspective view schematically illustrating an example of a conventional separation chip. FIG. 1-2 is a diagram as viewed from a thickness direction schematically illustrating the conventional separation chip illustrated in FIG. 1-1. FIG. 2 is a plan view schematically illustrating another example of the separation chip described in the below Comparative Example 2.

In the conventional separation chip illustrated in FIGS. 1-1 and 1-2, and in the separation chip according to Comparative Example 2 illustrated in FIG. 2, the suspension holding tank 1, the separation liquid holding tank 2, and the insoluble component holding tank 3 are connected and arranged in parallel in that order from the axis of rotation side. When the separation chip is rotated, of the suspension fed to the separation liquid holding tank 2 from the suspension holding tank 1 via the suspension introduction channel 6, the insoluble component is trapped in the insoluble component holding tank 3. However, at that point, the suspension has to pass through the narrow portion 10 between the separation liquid holding tank 2 and the insoluble component holding tank 3. When the suspension passes from the inner circumferential side (side towards the axis of rotation) of this narrow portion 10 to the outer circumferential side (side further away from the axis of rotation) due to centrifugal force, the insoluble component may block the narrow portion 10. Further, since the insoluble component in the suspension flows into the insoluble component holding tank 3 via the narrow portion 10 due to centrifugal force, there is no place for gases in the insoluble component holding tank 3 to escape. Consequently, there is the problem that gas bubbles tend to form in the insoluble component holding tank 3.

The tanks of our separation chip are connected so that a liquid can be fed by rotation in the order of the suspension holding tank 1, the insoluble component holding tank 3, and the separation liquid holding tank 2. Further, the separation chip has a mechanism in which a separation liquid or a suspension is fed from the insoluble component holding tank 3 on the outer circumferential side of the narrow portion 10 to the separation liquid holding tank 2 on the inner circumferential side thereof. Therefore, the insoluble component separated due to centrifugal force is directly trapped (held) in the insoluble component holding tank 3, so that blockages caused by the insoluble component at the narrow portion 10 do not occur. Further, the insoluble component holding tank 3 has at least two connecting portions including the narrow portion 10 and a connecting portion 11, which is opened on the insoluble component holding tank 3 side connecting with the suspension holding tank 1. Therefore, gases inside the insoluble component holding tank 3 in an amount equal to that of the suspension which flowed into the insoluble component holding tank 3 from the connecting portion 11 stably flows out to the separation liquid holding tank 2 via the narrow portion 10. Consequently, gas bubbles do not remain in the insoluble component holding tank 3. Therefore, separation of the insoluble component and the separation liquid can be stably carried out.

In our separation chip, the connecting portion 11 of the insoluble component holding tank 3 with the suspension holding tank 1 is positioned further toward the outer circumferential side than the narrow portion 10 between the separation liquid holding tank 2 and the insoluble component holding tank 3. The expression "further toward the outer circumferential side than the narrow portion 10" means that an object is positioned further toward the outer circumferential side than the opening of the narrow portion 10 on the insoluble component holding tank 3 side.

Furthermore, it is preferred that the connecting portion 11 of the insoluble component holding tank 3 and the suspension holding tank 1, specifically, the opening of the suspension introduction channel 6 on the insoluble component holding tank 3 side, is positioned on a wall face of the insoluble component holding tank 3 on the outer circumferential side. This allows the suspension to be even more effectively prevented from entering the separation liquid holding tank 2, and gas bubbles to be more effectively suppressed from remaining in the insoluble component holding tank 3. Here, "a wall face of the insoluble component holding tank 3 on the outer circumferential side" is, of the side wall of the insoluble component holding tank 3 when the separation chip is rotated, the wall face of the side wall positioned further toward the outer circumferential side.

The connection between the suspension holding tank 1 and the insoluble component holding tank 3 may be achieved by directly connecting these tanks to each other by an opening, or by connecting these tanks to each other by a suspension introduction channel 6, which is a tunnel shaped channel. Of these, it is preferred to connect by the suspension introduction channel 6. It is preferred to provide a suspension introduction channel 6 because the degree of freedom in the position and shape of the suspension holding tank 1 increases even when the connecting portion 11 of the insoluble component holding tank 3 with the suspension holding tank 1 is provided on a wall face of the insoluble component holding tank 3 on the outer circumferential side.

The suspension introduction channel 6 extends in an outer circumferential direction from the suspension holding tank 1 and is connected to and opens onto the insoluble component holding tank 3. The connecting portion 11 between the suspension introduction channel 6 and the insoluble component holding tank 3 has the same configuration as that already described for the connecting portion between the insoluble component holding tank 3 and the suspension holding tank 1. It is preferred that this connecting portion 11 is positioned further toward the outer circumferential side than the narrow portion 10 between the insoluble component holding tank 3 and the separation liquid holding tank 2. The connecting portion 11 is particularly preferably positioned on the wall face of the insoluble component holding tank 3 on the outer circumferential side. Positioning this connecting portion 11 further toward the outer circumferential side than the narrow portion 10 enables the separation of the insoluble component to smoothly proceed without blockages occurring or gas bubbles entering the insoluble component holding tank 3.

In the all of the configuration examples of the separation chip illustrated in FIGS. 3-1, 3-2, 4 and 5, the suspension introduction channel 6 is provided between the suspension holding tank 1 and the insoluble component holding tank 3. In the separation chips illustrated in FIGS. 3-1, 3-2, and 4, the connecting portion 11 between the suspension introduction channel 6 and the insoluble component holding tank 3, specifically, the opening of the suspension introduction channel 6 on the insoluble component holding tank 3 side, is positioned further toward the outer circumferential side than the narrow portion 10, and positioned on a side face of the upper end of the insoluble component holding tank 3 on the outer circumferential side.

In the separation chip illustrated in FIG. 5, the suspension introduction channel 6 merges with a below-described overflow channel 7, and then opens onto and is connected to the insoluble component holding tank 3 as a connecting portion 12. This connecting portion 12 is positioned further toward the outer circumferential side than the narrow portion 10, and is positioned on the side face of the insoluble component holding tank 3 on the outer circumferential side.

The size (diameter, channel length and the like) of the suspension introduction channel 6 is not especially limited, as long as the suspension can pass therethrough. The short diameter may be, for example, generally 10 to 1000 micrometers (μm), and preferably 50 to 500 micrometers. The length may be, for example, generally from 1 micrometer to 100 millimeters (mm), and preferably from 10 micrometers to 50 millimeters.

A channel may be provided which only allows a gas to pass between the suspension holding tank 1 and the separation liquid holding tank 2, and prevents a liquid such as a suspension or a separation liquid from passing through.

As described above, the separation liquid holding tank 2 and the insoluble component holding tank 3 are connected by the narrow portion 10. More specifically, the connecting portion of these tanks may be configured in a narrow constricting shape. These tanks may be connected by a narrow opening, or by a fine channel. In the configuration examples of the separation chip illustrated in FIGS. 3, 4, and 5, the narrow portion 10 is an opening which is in communication with the separation liquid holding tank 2 and the insoluble component holding tank 3. The narrow portion 10 has a cross-sectional short diameter generally of 5 micrometers to 5000 micrometers, and preferably 10 micrometers to 1000 micrometers. Since the narrow portion 10 preferably has a size through which the insoluble component in the suspension does not easily pass, it is preferred that the short diameter is in the range of 10 micrometers to 100 micrometers. Further, if the narrow portion 10 is a channel, it is preferred that the channel length is comparatively short, generally 10 micrometers to 10000 micrometers, and preferably 100 micrometers to 1000 micrometers.

In the insoluble component holding tank 3, the opening of the narrow portion 10 is preferably positioned at a high position. Consequently, when rotation is stopped, the insoluble component in the insoluble component holding tank 3, in the suspension introduction channel 6, and in the below-described overflow channel can be effectively prevented from entering the separation liquid holding tank 2. The expression "positioned at a high position" means that when rotation is stopped the opening is positioned in the upper half of the insoluble component holding tank 3. In particular, it is preferred that the opening of the narrow portion 10 is positioned on the upper side wall face of the insoluble component holding tank 3 on the inner circumferential side, as this makes it more difficult for the insoluble component having a larger specific gravity to flow out when rotation is stopped. Describing this using the configuration examples illustrated in FIGS. 4 and 5, of the wall face of the insoluble component holding tank 3, the constricted narrow portion 10 opens onto the upper wall face on the inner circumferential side as viewed from the axis of rotation.

A separation liquid discharge channel 4 may be provided for the separation liquid holding tank 2. The separation liquid discharge channel 4 has a function for discharging the separation liquid (liquid component) which has accumulated in the separation liquid holding tank 2 during rotation from the separation liquid holding tank 2, and even out of the separation chip, due to the action of gravity when rotation is stopped. It is preferred that the separation liquid discharge channel 4 extends from the separation liquid holding tank 2 in the direction of gravity, and also preferred that it extends in the direction of gravity toward the outer circumferential side. More specifically, it is preferred that the separation liquid discharge channel has an inflected portion which is inflected midway along a channel extending in the direction of gravity and in the outer circumferential direction with respect to the axis of rotation. This enables the separation liquid to be fed utilizing centrifugal force when again centrifuging. Consequently, the separation liquid can be prevented from flowing back or remaining, and can be efficiently recovered.

In the configuration examples illustrated in FIGS. 3-1, 3-2, and 4, the separation liquid discharge channel 4 is connected to the separation liquid holding tank 2. Furthermore, the separation liquid discharge channel 4 extends towards the outer circumferential side, and opens onto the outer wall of the separation chip on the outer circumferential side (in the configuration example illustrated in FIG. 4, a notch on a lower end portion of the chip on the outer circumferential side). In addition, in the configuration example illustrated in FIG. 5, a first portion area 4A of the separation liquid discharge channel 4 forms a common channel with a washing solution holding tank 5 and the separation liquid holding tank 2. At a second portion area 4B midway along this channel, a third portion area 4C, which is a latter half portion of the separation liquid discharge channel 4, is connected. The section formed from the portion areas 4A, 4B, and 4C of the separation liquid discharge channel 4 extends in the direction of gravity toward the outer circumferential side of the chip. Furthermore, the third portion area 4C of the separation liquid discharge channel 4 extends toward the outer circumferential side of the chip, and either opens onto the outer wall on the outer circumferential side or is in communication with a channel on a subsequent level.

It is preferred that the separation liquid discharge channel 4 of the separation chip has a section midway along the channel which has a smaller channel cross-sectional area than the channel cross-sectional area at the connecting portion with the separation liquid holding tank 2. More preferably, the separation liquid discharge channel 4 has a section midway along the channel having a channel cross-sectional area which becomes gradually smaller. Configuring so that the cross-sectional area of the separation liquid discharge channel 4 becomes gradually smaller allows capillary force (capillarity) to be utilized in addition to gravity. Consequently, the separation liquid can be discharged more efficiently in a shorter time.

Figure 5:
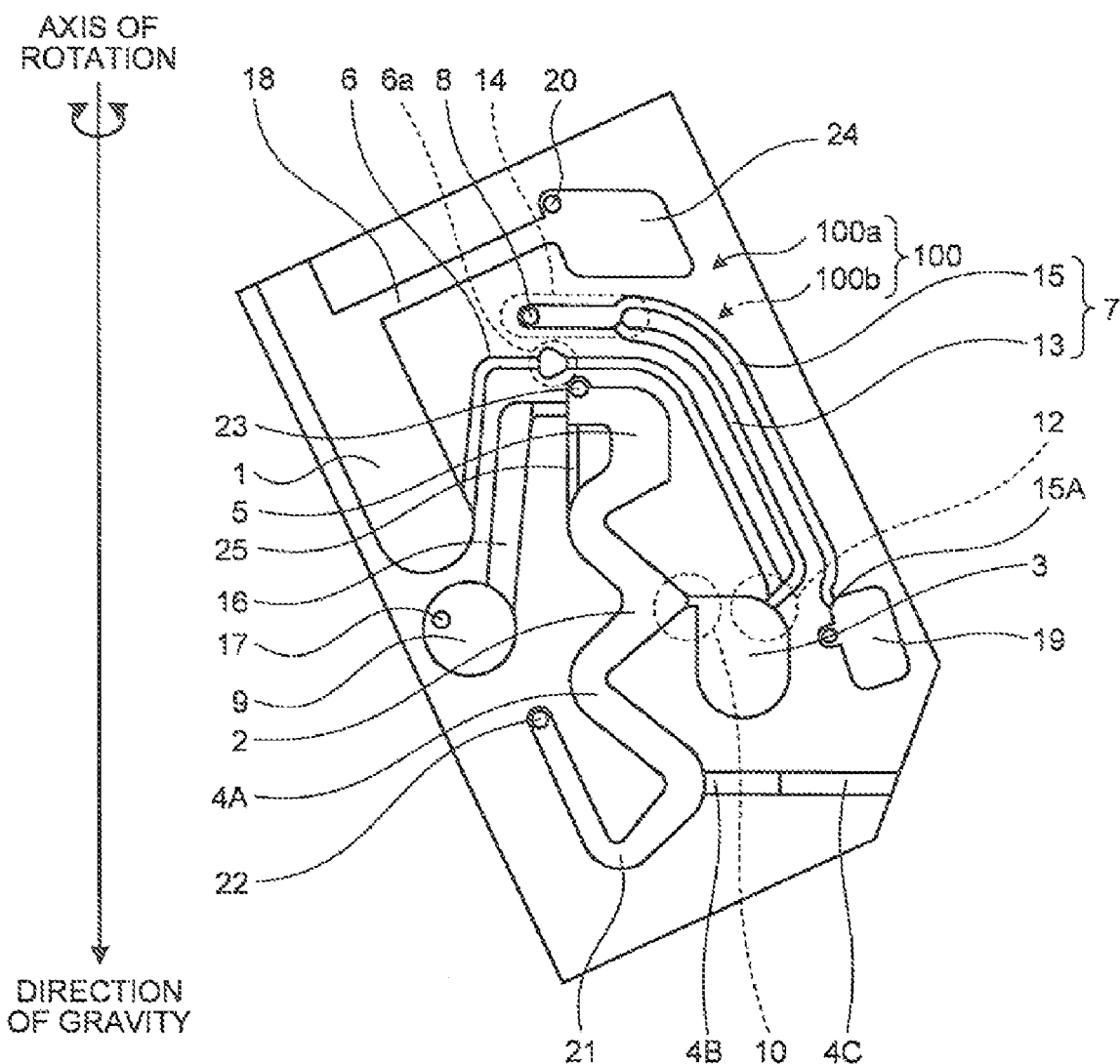
FIG. 5 is a plan view schematically illustrating another configuration example of a separation chip.

As illustrated in FIG. 5, the separation chip may have a washing solution holding tank 5. The washing solution holding tank 5 has a function for holding a washing solution during rotation, and discharging (supplying) the washing solution to the separation liquid holding tank 2 due to the action of gravity when rotation is stopped. Therefore, it is enough for the washing solution holding tank 5 to have a sufficient capacity for the washing solution to accumulate. A capacity in which, for example, about 10 microliters to 1000 microliters of washing solution may be accumulated is sufficient.

The washing solution holding tank 5 is provided above the separation liquid holding tank 2. It is preferred that the washing solution holding tank 5 and the separation liquid holding tank 2 are connected to each other by a channel. This enables the washing solution to be fed to the separation liquid holding tank 2 when rotation of the separation chip is stopped. In actual practice, it is sufficient for the washing solution holding tank 5 to be capable of temporarily holding the washing solution during rotation. Therefore, the washing solution holding tank 5 does not have to have a tank shape like the separation liquid holding tank 2. More specifically, the washing solution holding tank 5 may be a channel shape, or may be provided as a portion in a channel common to the washing solution holding tank 5 and the separation liquid holding tank 2.

In the configuration example of the separation chip illustrated in FIG. 5, the washing solution holding tank 5 is provided above the separation liquid holding tank 2. In this configuration example, the washing solution holding tank 5, the separation liquid holding tank 2, and the first portion area 4A of the separation liquid discharge channel 4 form a common channel. The section branching off from the second portion area 4B and the third portion area 4C of the separation liquid discharge channel 4 in this channel first extends downwards toward the inner circumferential side, then changes directions at a folded back portion 21, and extends upwards. Finally, this section comes to an end midway along to form an end section. A vent hole 22 opens onto the first main surface 100a side of the end section where the channel has come to an end.

The washing solution not only has a function for cleaning the separation liquid holding tank 2, but may also have a function for diluting the separation liquid. Further, the washing solution may have a function as a reagent which reacts with a specific component in the separation liquid. Specifically, the washing solution may include an antibody, an antigen, an enzyme, a nucleic acid and the like which reacts with a specific component in the separation liquid. For example, by using a labeled antibody as the washing solution, tank cleaning and an antigen-antibody reaction may be performed simultaneously. Specific examples of the washing solution include a solution containing a surfactant, a solution containing a stabilizing agent such as glycerol, a protein solution containing a labeled antibody, a labeled antigen, or an enzyme, an enzyme reaction substrate solution and the like.

A washing solution storage tank 9 connected to the washing solution holding tank 5 may be provided. By providing the washing solution storage tank 9, there is no need to pre-hold the washing solution in the washing solution holding tank 5. Therefore, if a washing solution storage tank 9 is provided, because the washing solution holding tank 5 only needs to be capable of holding the washing solution during rotation, the degree of freedom of the size and shape of the washing solution holding tank 5 increases. The size of the washing solution storage tank 9 may be appropriately determined in a range capable of storing the washing solution. It is sufficient for the washing solution storage tank 9 to be capable of accumulating 10 microliters to 1000 microliters of washing solution. Generally, the tank has a capacity of 20 microliters to 1500 microliters, and preferably 50 microliters to 500 microliters. The washing solution holding tank 5 and the washing solution storage tank 9 may be connected by an opening which is in communication with each of the tanks, or, as illustrated in FIG. 5, connected by a washing solution introduction channel 16.

In the configuration example of the separation chip illustrated in FIG. 5, the washing solution storage tank 9 is provided below and on the inner circumferential side of the washing solution holding tank 5. The washing solution holding tank 5 and the washing solution storage tank 9 are connected by the washing solution introduction channel 16 which extends upwards and toward the outer circumferential side from the washing solution storage tank 9. Vent holes 17 and 23 which open onto the first main surface 100a are provided in the washing solution storage tank 9 and the washing solution holding tank 5, respectively. The washing solution storage tank 9 is positioned on the inner circumferential side of the washing solution holding tank 5. The washing solution storage tank 9 is connected to the washing solution holding tank 5 with the washing solution introduction channel 16. Therefore, the washing solution pre-stored in the washing solution storage tank 9 flows via the washing solution introduction channel 16 to the washing solution holding tank 5 due to the centrifugal force by rotation, and is held there. Further, providing the vent hole 17 in the washing solution storage tank 9 allows the movement of the washing solution from the washing solution storage tank 9 to the washing solution holding tank 5 due to centrifugal force to be efficiently carried out. By stopping rotation, the washing solution held in the washing solution holding tank 5 can clean the separation liquid holding tank 2. Further, stopping rotation also allows the separation liquid accumulated in the separation liquid holding tank 2 to be pushed out to the separation liquid discharge channel 4 extending in the direction of gravity. In addition, providing the vent hole 23 in the washing solution holding tank 5 allows the movement of the washing solution in the direction of gravity caused by stopping rotation to be efficiently carried out. In the separation chip illustrated in FIG. 5, when the washing solution moves from the washing solution holding tank 5 to the separation liquid holding tank 2, to efficiently carry out the movement of the washing solution, a gas channel 25 linking the separation liquid holding tank 2 and the washing solution holding tank 5 is provided for moving a gas.

As illustrated in FIG. 5, for example, the separation chip may have overflow channels 18 and 7, which are connected to the suspension holding tank 1 and the insoluble component holding tank 3, respectively. When the suspension in the suspension holding tank 1 is fed to the insoluble component holding tank 3 and the separation liquid holding tank 2 by rotation, the overflow channels 18 and 7 regulate the amount of fed suspension or the liquid surface formed in the separation liquid holding tank 2 during rotation. Thus, the overflow channels 18 and 7 are channels for providing a function of regulating the amount of the separation liquid isolated and recovered when rotation is stopped. Providing the overflow channels 18 and 7 in connection with the suspension holding tank 1 and the insoluble component holding tank 3 allows the amount of isolated and recovered separation liquid to be kept constant regardless of the amount of suspension in the suspension holding tank 1. Consequently, a quantitative performance can be secured.

The separation chip may be provided with tanks, specifically, overflow holding tanks 19 and 24, which are connected to the overflow channels 18 and 7 for holding suspension which has overflowed. The positions of the overflow holding tanks 19 and 24 are not especially limited. Generally, the overflow holding tanks 19 and 24 can be provided on the outer circumferential side of the overflow channels 18 and 7.

The overflow channel 7 extends toward the inner circumferential side from the connecting portion 12 with the suspension introduction channel 6 or the insoluble component holding tank 3, and then folds back toward the outer circumferential side at the folded back portion 14. Consequently, during chip rotation, the liquid surface formed in the separation liquid holding tank 2 and the folded back portion 14 of the overflow channel 7 are defined on the same circumferential plane. This allows the height of the liquid surface in the separation liquid holding tank 2 to be regulated at a constant level.

It is preferred that the overflow channel 7 has a configuration which first extends toward the inner circumferential side from the connecting portion 12 with the suspension introduction channel 6 or the insoluble component holding tank 3, and then folds back toward the outer circumferential side in the direction of gravity. By configuring in such a manner, liquid in the overflow channel 7 further on from the folded back portion 14 and liquid which has moved to a tank further along therefrom can be prevented from flowing back to the suspension introduction channel 6 or the insoluble component holding tank 3 by the action of gravity when rotation is stopped. Consequently, a quantitative performance can be secured and the insoluble component can be effectively prevented from entering the separation liquid holding tank 2.

The overflow channels in the configuration example of the separation chip illustrated in FIG. 5 will now be described in more detail. The overflow channel 7 is connected to the suspension introduction channel 6 by the connecting portion 12. A first half portion 13 of the overflow channel 7 first extends upwards and toward the inner circumferential side from the connecting portion 12. Then, from the folded back portion 14, a latter half portion 15 of the overflow channel 7 extends downwards and toward the outer circumferential side. The latter half portion 15 is connected with the overflow holding tank 19 which stores suspension which has overflowed at an end section 15A positioned approximately parallel with the connecting portion 12.

It is preferred that the overflow channel 7 has a vent hole 8 opening onto the main surface 100 on the inner circumferential side of the folded back portion 14. By providing the vent hole 8 in the folded back portion 14, the occurrence of siphoning from suspension which has filled the overflow channel 7 during rotation can be completely suppressed. Consequently, the separation liquid and the suspension can be prevented from flowing out from the separation liquid holding tank 2 and the insoluble component holding tank 3.

When the vent hole 8 is provided in the folded back portion 14, the liquid in the first half portion 13 of the overflow channel 7 extending toward the inner circumferential side until the folded back portion 14 may flow back into the suspension introduction channel 6 or the insoluble component holding tank 3 when rotation is stopped. To prevent this, it is preferred that the capacity of the overflow channel 7 extending toward the inner circumferential side until the folded back portion 14 is smaller than the capacity of the insoluble component holding tank 3. For example, the overflow channel 7 extending toward the inner circumferential side may be configured so that its capacity is generally 20% or less, and preferably 10% or less, the capacity of the insoluble component holding tank 3. Further, the separation chip is preferably configured so that the solution in the first half portion 13 of the overflow channel 7 when rotation is stopped continues to be held by surface tension and does not flow back to the insoluble component holding tank 3 or the suspension introduction channel 6. Therefore, it is preferred that the cross-section of the first half portion 13 of the overflow channel 7 is small, and generally 0.3 square millimeters or smaller, and preferably 0.1 square millimeters or smaller.

As illustrated in FIG. 5, the vent hole 8 is provided on a tip end portion extending toward the inner circumferential side of the folded back portion 14 of the overflow channel 7. In this example, the capacity of the first half portion 13 of the overflow channel 7 is small, only about 5% of the capacity of the insoluble component holding tank 3.

An overflow channel 18 connected to the suspension holding tank 1 may also be provided. This allows the amount of isolated and recovered separation liquid to be kept constant regardless of the amount of suspension in the suspension holding tank 1. Consequently, a quantitative performance can be secured. By combining this overflow channel 18 and the above-described overflow channel 7 which is connected to the suspension introduction channel 6 or the insoluble component holding tank 3, the amount of suspension can be more effectively regulated.

The connecting portion between the suspension holding tank 1 and the overflow channel 18 is positioned above the connecting portion 12 between the suspension holding tank 1 and the insoluble component holding tank 3. When the suspension introduction channel 6 is provided, this connecting portion is also positioned above the connecting portion between the suspension introduction channel 6 and the suspension holding tank 1. Unlike the overflow channel 7 connected to the suspension introduction channel 6 and the insoluble component holding tank 3, the overflow channel 18 connected to the suspension holding tank 1 is different in that it has a function for preventing the suspension from flowing out from the separation chip due to centrifugal force (rotation) when a large amount of suspension is placed in the suspension holding tank 1.

As illustrated in FIG. 5, the overflow channel 18 is connected to the suspension holding tank 1. The connecting portion is positioned above the suspension introduction channel 6. An overflow holding tank 24 for storing suspension which has overflowed is connected to an end portion on the outer circumferential side of the overflow channel 18. A vent hole 20 is provided in the overflow holding tank 24.

Another configuration example of the separation chip will now be described with reference to FIGS. 6-1, 6-1, 6-3, and 6-4.

Figures 1, 6:
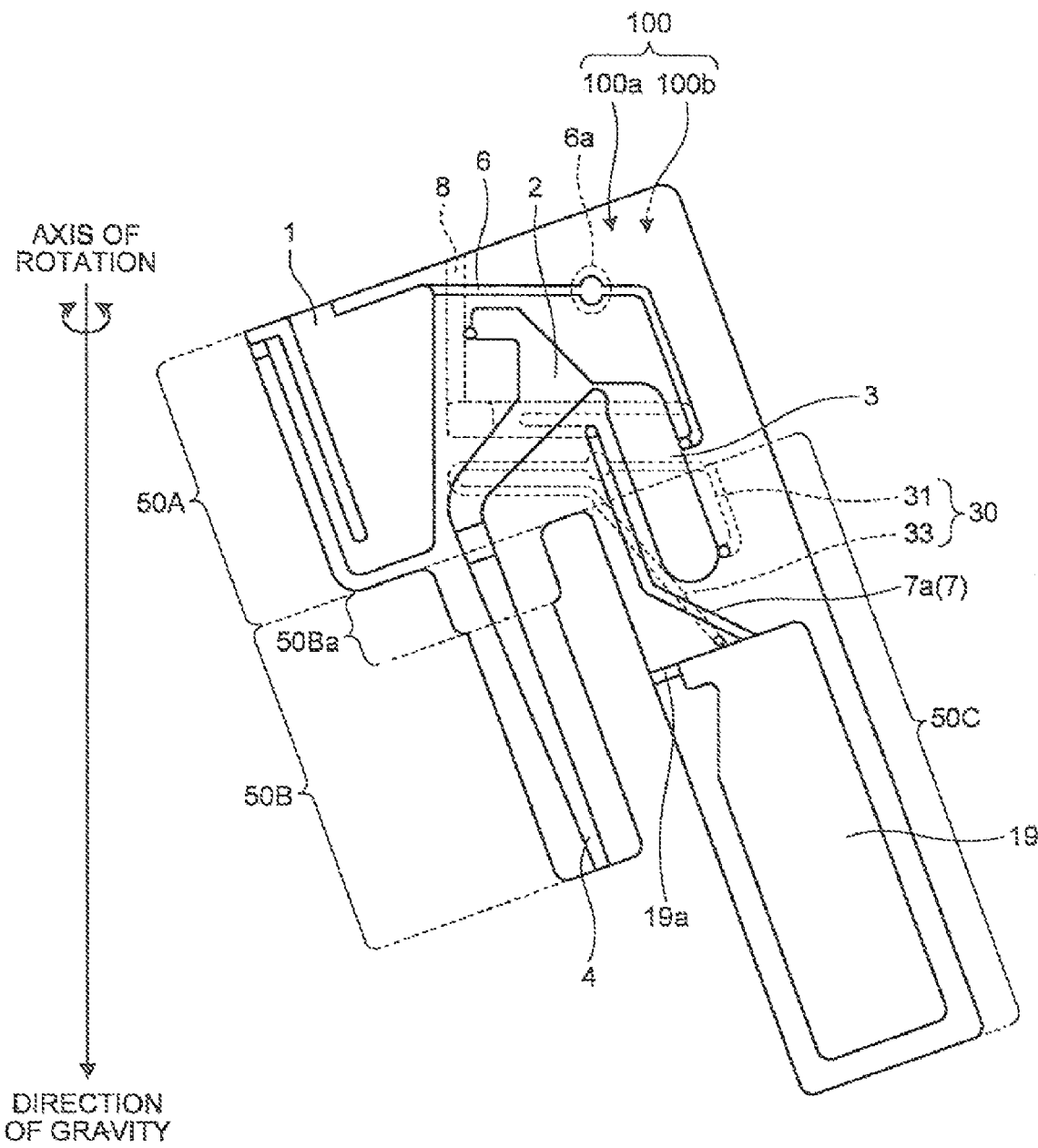
Figures 2, 6:
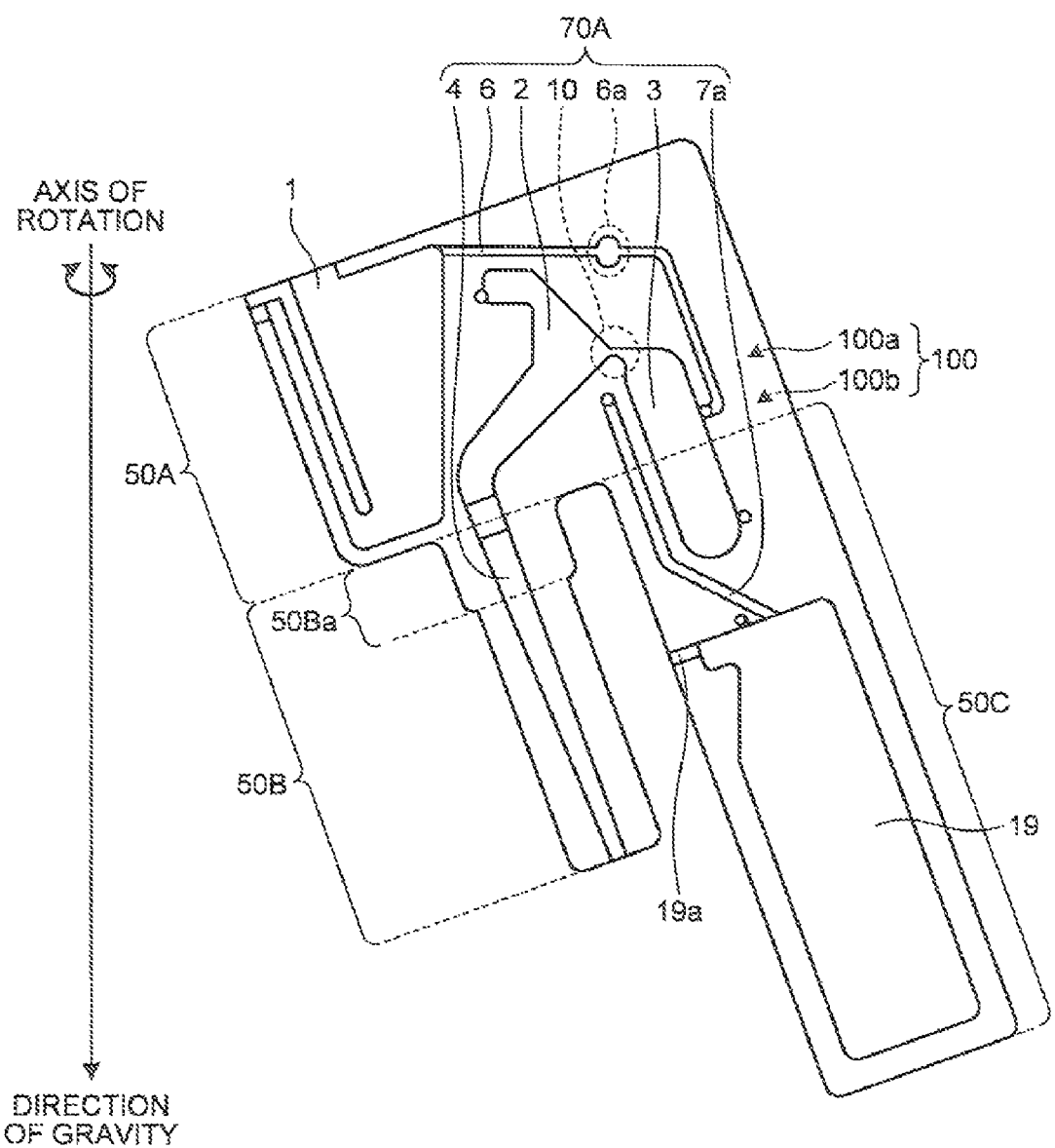
Figures 4, 6:
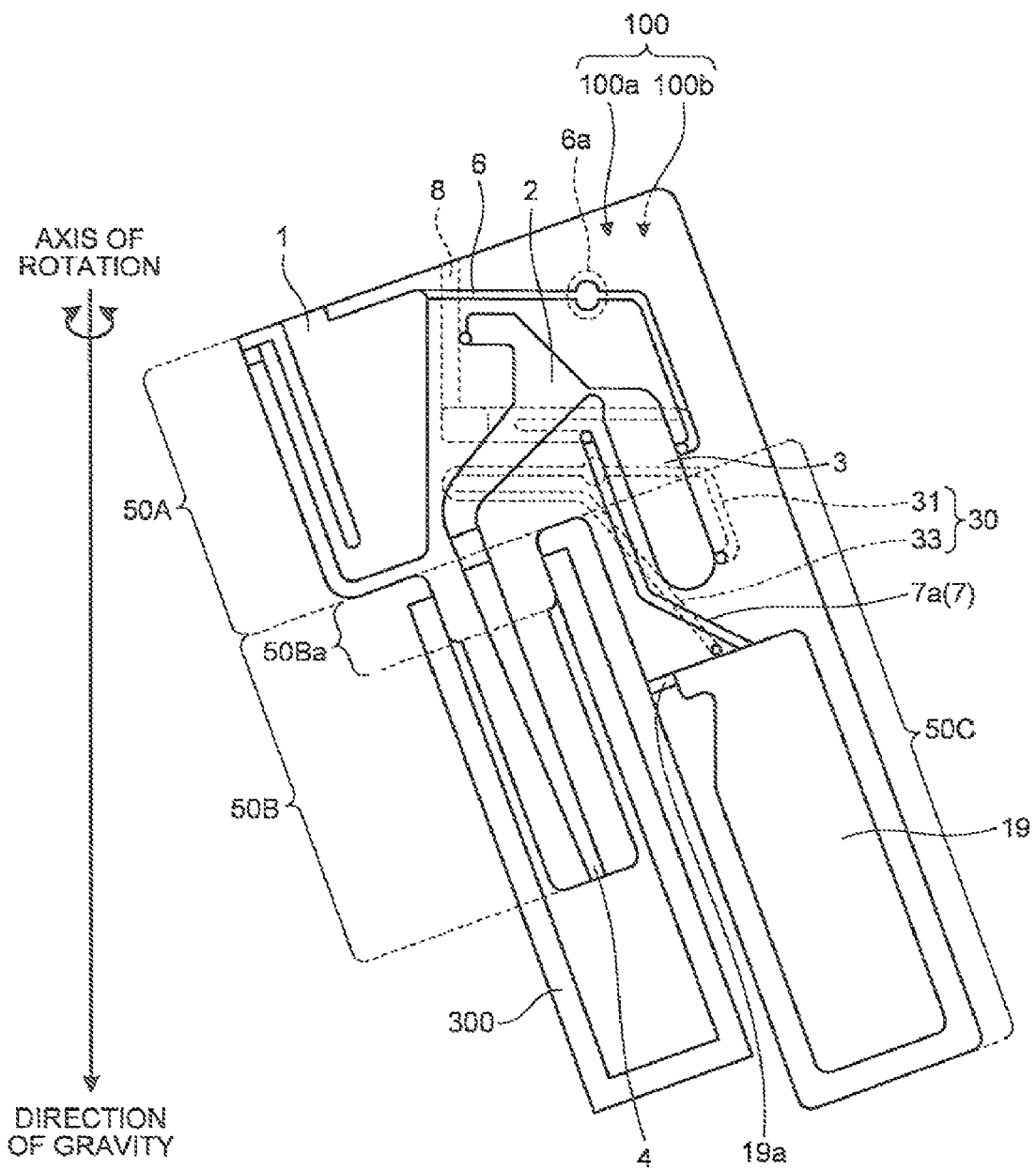

FIG. 6-1 is a plan view (1) transparently illustrating another configuration example of the separation chip. FIG. 6-2 is a plan view (2) transparently illustrating another configuration example of a separation chip following on from FIG. 6-1. FIG. 6-3 is a plan view (3) transparently illustrating another configuration example of a separation chip following on from FIG. 6-2. FIG. 6-4 is a plan view (4) transparently illustrating another configuration example of a separation chip following on from FIG. 6-3.

As illustrated in FIGS. 6-1, 6-2, and 6-3, the separation chip according to this configuration example is provided with a first channel group 70A (see FIG. 6-2) arranged near the first main surface 100a, and a second channel group 70B (see FIG. 6-3, represented by the dashed line in FIG. 6-1) arranged near the second main surface 100b so as to lie over the first channel group 70A in a thickness direction of the separation chip. The boundary of an integral channel which connects the first channel group 70A and the second channel group 70B may be represented by a white on black circle.

The first channel group 70A is arranged near the first main surface 100a so as to lie over the second channel group 70B in a thickness direction of the separation chip.

The first channel group 70A has a separation liquid holding tank 2, an insoluble component holding tank 3 connected with the separation liquid holding tank 2 by a narrow portion 10, a separation liquid discharge channel 4 connected to a lower end portion of the separation liquid holding tank 2, a suspension introduction channel 6 connecting a suspension holding tank 1 and the insoluble component holding tank 3, and a first overflow channel portion 7a. One end of the first overflow channel portion 7a is connected to an overflow holding tank 19.

The separation chip has two protrusions having different protruding lengths from a base portion 50A when the separation chip is viewed with the suspension holding tank 1 positioned on the bottommost side. Consequently, the separation chip has an overall shape like the letter "F." In this example, the separation chip has a first protrusion 50B and a second protrusion 50C extending from the base portion 50A in the same direction. The extension length of the second protrusion 50C is longer than the first protrusion 50B.

By configuring in this way, as described below, it is easier to mount a separate separation liquid recovery container, for example. Further, by utilizing the space between the protrusions when mounting such a separation liquid recovery container, additional functions can be added to the separation chip without increasing the overall size of the chip.

The separation liquid holding tank 2 has an approximately reverse C shape. The insoluble component holding tank 3 is connected with a reverse C inflected portion of the separation liquid holding tank 2 by the narrow portion 10. The separation liquid discharge channel 4 becomes gradually smaller heading towards the tip end. The separation liquid discharge channel 4 inflects to the outer circumferential side midway along the channel, then extends downwards (direction of gravity) in a straight line, and opens onto the outside of the separation chip.

As illustrated in FIG. 6-4, a separation liquid recovery container 300 separate from the separation chip may be mounted on the first protrusion 50B, in which the separation liquid discharge channel 4 extends. The separation liquid recovery container 300 accumulates in its interior the separation liquid which flows out of the separation chip from the separation liquid discharge channel 4.

In this example, the separation liquid recovery container 300 is in the form of a container having a rectangular appearance, with only its upper face open. The separation liquid recovery container 300 has a hollow in its thickness in which the separation liquid can accumulate.

In this example, the separation liquid discharge channel 4 extends in the interior of the first protrusion 50B, and opens onto a tip end portion of the first protrusion 50B. The separation liquid recovery container 300 is configured to house the first protrusion 50B in a hollow, and accumulate the separation liquid which flows out in the hollow. At this stage, it is preferred that the separation liquid recovery container 300 and the first protrusion 50B are engaged with each other in a detachable manner. In this example, the separation liquid recovery container 300 and the first protrusion 50B are engaged with each other in a detachable manner by forming the base portion 50A vicinity of the first protrusion 50B, specifically, a portion area 50Ba on the opposite side of the tip end portion, slightly fatter than the other areas.

Furthermore, the suspension introduction channel 6 has a knob-like stop valve 6a midway along the channel.

The second channel group 70B has a second overflow channel portion 7b which is connected with a first overflow channel portion 7a, an insoluble component discharge channel 30 which is connected with the insoluble component holding tank 3, and a vent hole 8 which is connected with the second overflow channel portion 7b and which extends upwards and opens onto the outside of the separation chip. The second overflow channel portion 7b integrally forms the overflow channel 7 with the first overflow channel portion 7a.

The insoluble component discharge channel 30 is connected so as to open onto a wall face on the outer circumferential side at a position lower than the connecting portion of the insoluble component holding tank 3 with the suspension introduction channel 6. The insoluble component discharge channel 30 is formed from a first half portion 31 extending toward the inner circumferential side, a folded back portion 32, and a latter half portion 33 extending toward the outer circumferential side. The first half portion 31 is connected to the folded back portion 32 by first extending upwards, then inflecting and extending toward the inner circumferential side with respect to the insoluble component holding tank 3 so as to pass through the second main surface 100b side. The folded back portion 32 is inflected in a U shape, and connects the half portion 31 extending toward the inner circumferential side with the latter half portion 33 extending toward the outer circumferential side. More specifically, the insoluble component discharge channel 30 extending toward the inner circumferential side from the wall face of the insoluble component holding tank 3 on the outer circumferential side is folded back by the folded back portion 32, thereby changing directions to extend toward the outer circumferential side. The latter half portion 33 extending toward the outer circumferential side is inflected further down (direction of gravity), and is connected to the overflow holding tank 19.

The second overflow channel portion 7b is connected so that one end opens onto a wall face of the insoluble component holding tank 3 on the outer circumferential side. At this stage, the second overflow channel portion 7b is integrally connected with the suspension introduction channel 6 to a wall face of the insoluble component holding tank 3 on the outer circumferential side. The second overflow channel portion 7b is connected to a folded back portion 14 by first extending upwards from the outer circumferential side of the insoluble component holding tank 3, then inflecting and extending toward the inner circumferential side with respect to the insoluble component holding tank 3 so as to pass through the second main surface 100b side. The folded back portion 14 folds the second overflow channel portion 7b extending toward the inner circumferential side back to the outer circumferential side, thereby changing the direction of the second overflow channel portion 7b. The other end of the second overflow channel portion 7b folded back toward the outer circumferential side is inflected in a direction facing the first main surface 100a, and is connected to the other end of the first overflow channel portion 7a. More specifically, the overflow channel 7 connects the insoluble component holding tank 3 and the overflow holding tank 19.

The vent hole 8 is connected to an end portion of the folded back portion 14. In this example, the vent hole 8 opens onto an upper side surface which is sandwiched between the first main surface 100a and the second main surface 100b.

The second overflow channel portion 7b and the first half portion 31 of the insoluble component discharge channel 30 are arranged approximately in parallel. Furthermore, the folded back portion 32 of the insoluble component discharge channel 30 is arranged further toward the inner circumferential side than the folded back portion 14 of the overflow channel 7.

A vent hole 19a is provided on the second protrusion 50C in which the overflow holding tank 19 is arranged. The vent hole 19a extends from an upper end portion of the overflow holding tank 19 toward the inner circumferential side, and opens onto an edge on the inner circumferential side of the second protrusion 50C. This vent hole 19a has a function for letting gases in the overflow holding tank 19 escape from the separation chip.

The insoluble component discharge channel 30 has a function for discharging from the insoluble component holding tank 3 a component including an insoluble component held in the insoluble component holding tank 3 (suspension having a high ratio of insoluble component). This enables the mixing of the insoluble component with the separation liquid to be more effectively prevented.

Especially when discharging the separation liquid by gravity, the suspension in the suspension introduction channel 6 and the overflow channel 7 flows to the insoluble component holding tank 3 due to the action of gravity. Consequently, there is still a probability that suspension containing the insoluble component may enter the separation liquid holding tank 2. However, by providing the insoluble component discharge channel 30, the mixing of the insoluble component with the separation liquid can be more effectively suppressed.

Further, when again performing a rotation operation to completely discharge the separation liquid and the like after the separation liquid is discharged by gravity, the liquid surface of the suspension in the suspension introduction channel 6 or the overflow channel 7 moves further toward the outer circumferential side than during the initial rotation. Therefore, there is still a probability that the separation liquid in the suspension introduction channel 6, the overflow channel 7, or the insoluble component holding tank 3 may flow into the separation liquid holding tank 2. Consequently, when rotation is again stopped, the separation liquid may again be discharged due to gravity, which can harm separation liquid quantitative performance and analysis accuracy. Therefore, by providing the insoluble component discharge channel 30, flow of the separation liquid to the separation liquid holding tank 2 due to further rotation can be effectively suppressed. Consequently, harm to separation liquid quantitative performance and analysis accuracy can be prevented.

The insoluble component discharge channel 30 is a channel for causing capillarity. It is sufficient for the insoluble component discharge channel 30 to have one end which is connected further toward the outer circumferential side than the narrow portion 10. Preferably, the insoluble component discharge channel 30 is connected to the suspension introduction channel 6 or the overflow channel 7, or the insoluble component holding tank 3 further toward the outer circumferential side than the narrow portion 10. Most preferably, the insoluble component discharge channel 30 is connected to a wall of the insoluble component holding tank 3 on the outer circumferential side. This allows the insoluble component to be completely discharged.

The other end of the insoluble component discharge channel 30 may also be connected to any of the vent holes, channels, tanks and the like. However, it is preferred that the insoluble component discharge channel 30 is connected to a waste tank. The insoluble component discharge channel 30 may be connected with the overflow holding tank 19. In such a case, the overflow holding tank 19 may also act as the waste tank, which allows the required number of tanks to be reduced, and the separation chip to be made more compact.

It is preferred that the insoluble component discharge channel 30 has a configuration which first extends from the connecting portion with the insoluble component holding tank 3 toward the inner circumferential side, and then folds back to the outer circumferential side. With such a configuration, during an initial rotation, the insoluble component can be allowed to remain in the insoluble component holding tank 3. Further, the insoluble component can be discharged by capillarity when rotation is stopped and by a siphon effect during further rotation. More preferably, the insoluble component discharge channel 30 is configured so that the folded back portion 32 is arranged further toward the inner circumferential side than the folded back portion 14 of the overflow channel 7. According to this configuration, even if the amount of suspension is excessive, the amount of liquid can be accurately regulated because excessive suspension is discarded via the overflow channel 7 during rotation. In addition, the liquid surface in the insoluble component discharge channel 30 can be reliably positioned in the channel extending toward the inner circumferential side. Subsequently, due to capillarity produced by the insoluble component discharge channel 30 when rotation is stopped, the suspension containing the insoluble component flows past the folded back portion 32, and fills the latter half portion 33, which is a channel extending toward the outer circumferential side. Then, due to a siphon effect produced during subsequent rotation, the insoluble component can be discharged to the overflow holding tank 19, for example.

It is preferred that the folded back portion 32 of the insoluble component discharge channel 30, specifically, the folded back portion 32 connecting the first half portion 31 extending toward the inner circumferential side and the latter half portion 33 extending toward the outer circumferential side, is positioned above the narrow portion 10 positioned between the insoluble component holding tank 3 and the separation liquid holding tank 2. According to this configuration, during the period of carrying out rotation until rotation is stopped, the suspension in the insoluble component discharge channel 30 can be prevented from going past the folded back portion 32 of the insoluble component discharge channel 30. Consequently, a siphon effect is prevented from being expressed in the steps of from rotation until rotation is stopped. This allows the possibility of the separation liquid which is to be isolated being discharged along with the insoluble component to be eliminated.

It is preferred that the insoluble component discharge channel 30 has midway along the channel a knob-like stop valve 31a whose channel cross-sectional area (diameter) increases. The stop valve 31a in the insoluble component discharge channel 30 is preferably positioned further downstream than the latter half portion 33 which is folded back toward the outer circumferential side of the insoluble component discharge channel 30, and positioned further toward the outer circumferential side than the narrow portion 10. The suspension containing a large amount of insoluble component when rotation is stopped flows as far as the stop valve 31a by capillarity, where it accumulates. Therefore, by providing the stop valve 31a, the amount of suspension flowing through the insoluble component discharge channel 30 can be reduced, thereby preventing the recovery ratio of the separation liquid from being harmed.

An example of operation of the separation chip having the configuration described using FIGS. 6-1, 6-2, and 6-3 will now be described with reference to FIGS. 7-1, 7-2, 7-3, and 7-4.

Figures 1, 7:
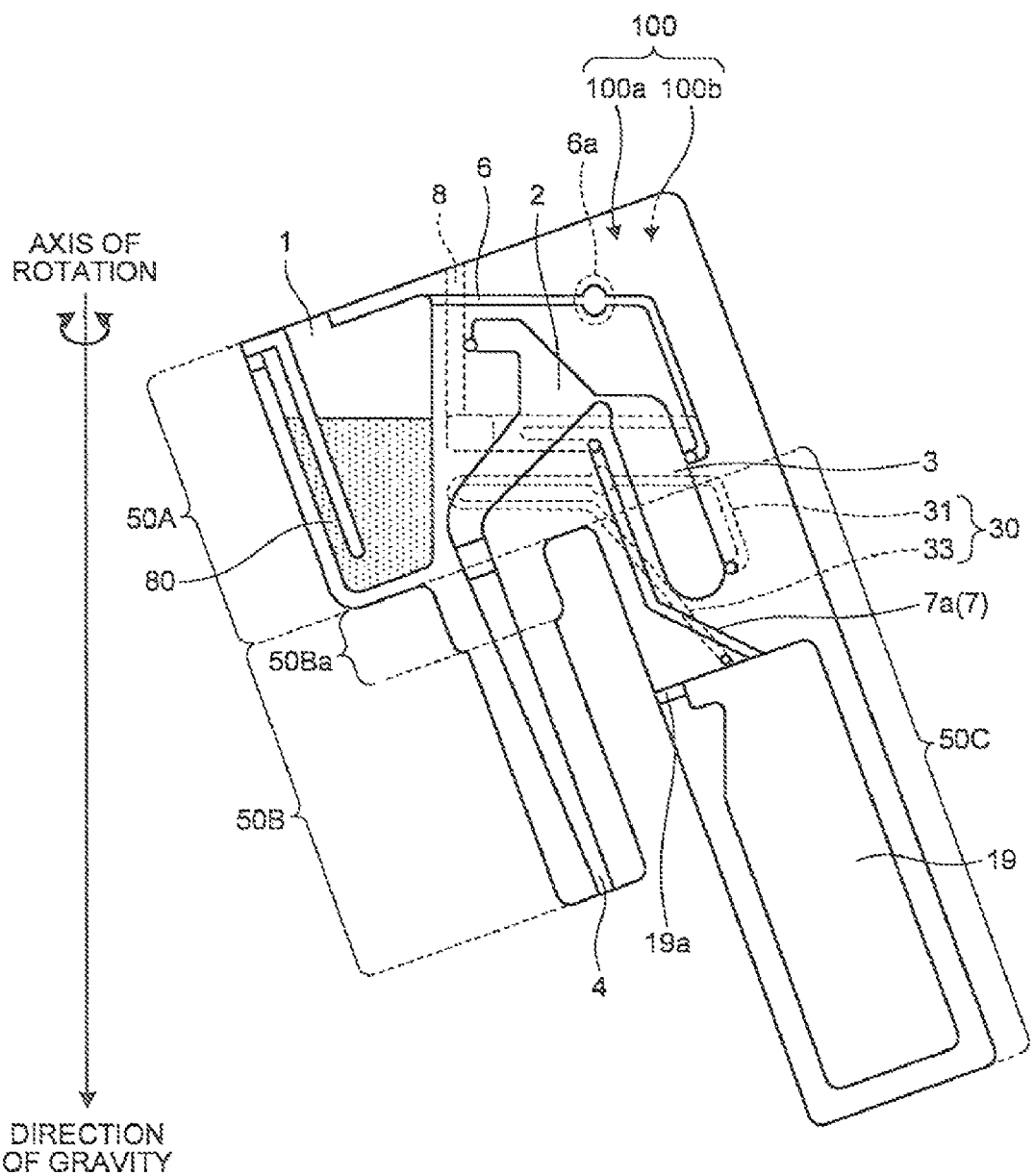
Figures 3, 7:
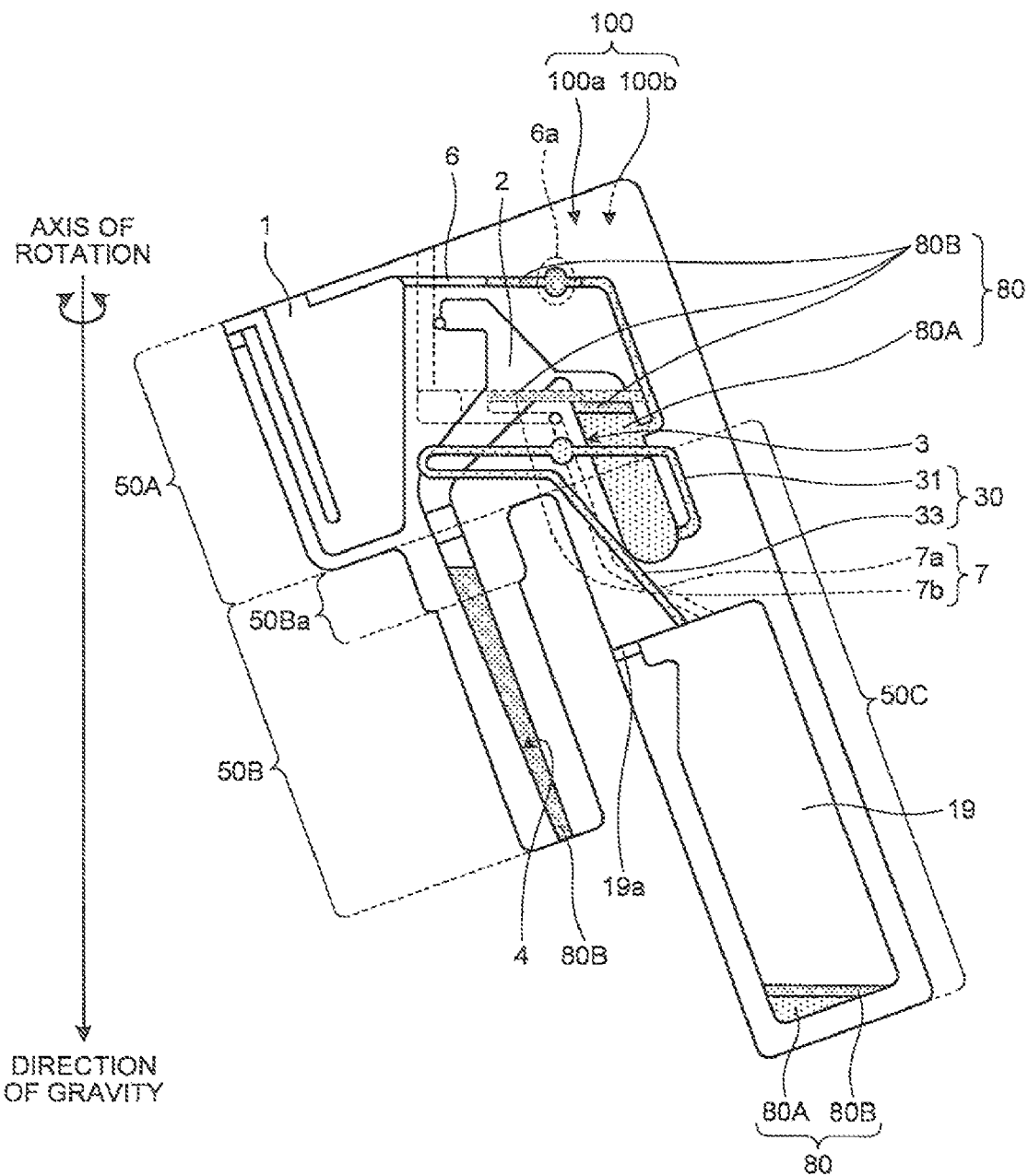

FIG. 7-1 is a schematic view (1) illustrating the operation (state in which rotation is stopped) of a separation chip. FIG. 7-2 is a schematic view (2) illustrating the operation (during initial rotation) of a separation chip. FIG. 7-3 is a schematic view (3) illustrating the operation (state in which rotation is stopped) of a separation chip. FIG. 7-4 is a schematic view (4) illustrating the operation (during further rotation) of a separation chip.

As illustrated in FIG. 7-1, in a state where rotation is stopped, a suspension 80 is introduced into the suspension holding tank 1 of the separation chip. At this stage, the flow of the suspension 80 to the insoluble component holding tank 3 can be prevented by the stop valve 6a provided in the suspension introduction channel 6.

As illustrated in FIG. 7-2, when the separation chip starts to rotate due to an initial rotation operation, the suspension 80 is fluidly fed via the suspension introduction channel 6 and introduced into the insoluble component holding tank 3. The suspension 80 is separated by the centrifugal force generated by rotation into an insoluble component 80A and a liquid component 80B. The insoluble component 80A mainly adheres to a side wall on the outer circumferential side of the insoluble component holding tank 3. The liquid component 80B overflows from the insoluble component holding tank 3, and is introduced (fed) into the separation liquid holding tank 2 via the narrow portion 10 from the outer circumferential side. Excess suspension 80 is discharged (fed) to the overflow holding tank 19 by the overflow channel 7. At this stage, the liquid surfaces in the separation liquid holding tank 2, in the suspension introduction channel 6, and in the insoluble component discharge channel 30 are all defined in an approximately vertical plane of the folded back portion 14 of the overflow channel 7. Then, after separating the insoluble component 80A and the liquid component 80B of the suspension 80 by utilizing centrifugal force generated by rotation, rotation is stopped.

A separation operation will now be described for when the difference between the specific gravity of the insoluble component in the suspension and the specific gravity of the liquid component is small. When the separation chip starts to rotate due to an initial rotation operation, the suspension 80 is fluidly fed via the suspension introduction channel 6 and introduced into the insoluble component holding tank 3. The suspension 80 overflows from the insoluble component holding tank 3, and is introduced (fed) into the separation liquid holding tank 2 via the narrow portion 10 from the outer circumferential side. Excess suspension 80 is discharged (fed) to the overflow holding tank 19 by the overflow channel 7. At this stage, the liquid surface in the separation liquid holding tank 2, in the suspension introduction channel 6, and in the insoluble component discharge channel 30 are all defined in an approximately vertical plane of the folded back portion 14 of the overflow channel 7. The suspension 80 is progressively separated by the centrifugal force generated by rotation into an insoluble component 80A and a liquid component 80B. The insoluble component 80A mainly adheres to a side wall of the insoluble component holding tank 3 on the outer circumferential side. The liquid component 80B is mainly held in the separation liquid holding tank 2. Then, after separating the insoluble component 80A and the liquid component 80B of the suspension 80 by utilizing centrifugal force generated by rotation, rotation is stopped.

As illustrated in FIG. 7-3, after rotation of the separation chip is stopped, the portion of the separation liquid held in the separation liquid holding tank 2, specifically, the liquid component 80B, falls down in the separation liquid discharge channel 4 due to the action of gravity, and moves toward the outer circumferential side to below the inflected portion. As described above, the separation liquid discharge channel 4 has a section midway along the channel which has a smaller channel cross-sectional area than the channel cross-sectional area at the connecting portion with the separation liquid holding tank 2. This cross-sectional area becomes gradually smaller in the direction of gravity, which is the extension direction. Consequently, capillary force (capillarity) can be used in addition to gravity, so that the separation liquid is made to fall in the direction of gravity in a shorter time. Further, the separation liquid discharge channel 4 is inflected toward the outer circumferential side midway along the channel, and has a section extending toward the outer circumferential side in the direction of gravity. Thus, if the separation liquid discharge channel 4 is configured to be a channel inflected to the outer circumferential side, in the separation liquid discharge channel 4, the liquid component 80B accumulates at the section extending to the outer circumferential side in the direction of gravity.

At this stage, the suspension 80 containing a large amount of insoluble component 80A proceeds through the insoluble component discharge channel 30 by capillarity, then passes through, in order, the first half portion 31, the folded back portion 32, and the latter half portion 33 of the insoluble component discharge channel 30 to fill the insoluble component discharge channel 30.

As illustrated in FIG. 7-4, due to the centrifugal force generated by further rotation, the liquid component 80B which has accumulated in the separation liquid discharge channel 4 positioned below the section inflected toward the outer circumferential side is completely discharged out of the separation chip from the separation liquid discharge channel 4 extending toward the outer circumferential side by the action of centrifugal force. The suspension 80 containing a large amount of insoluble component 80A in the insoluble component holding tank 3 passes through the insoluble component discharge channel 30, and in this example, due to a siphon effect, is completely discharged (fed) to the overflow holding tank 19 also acting as a waste tank.

Figure 8:
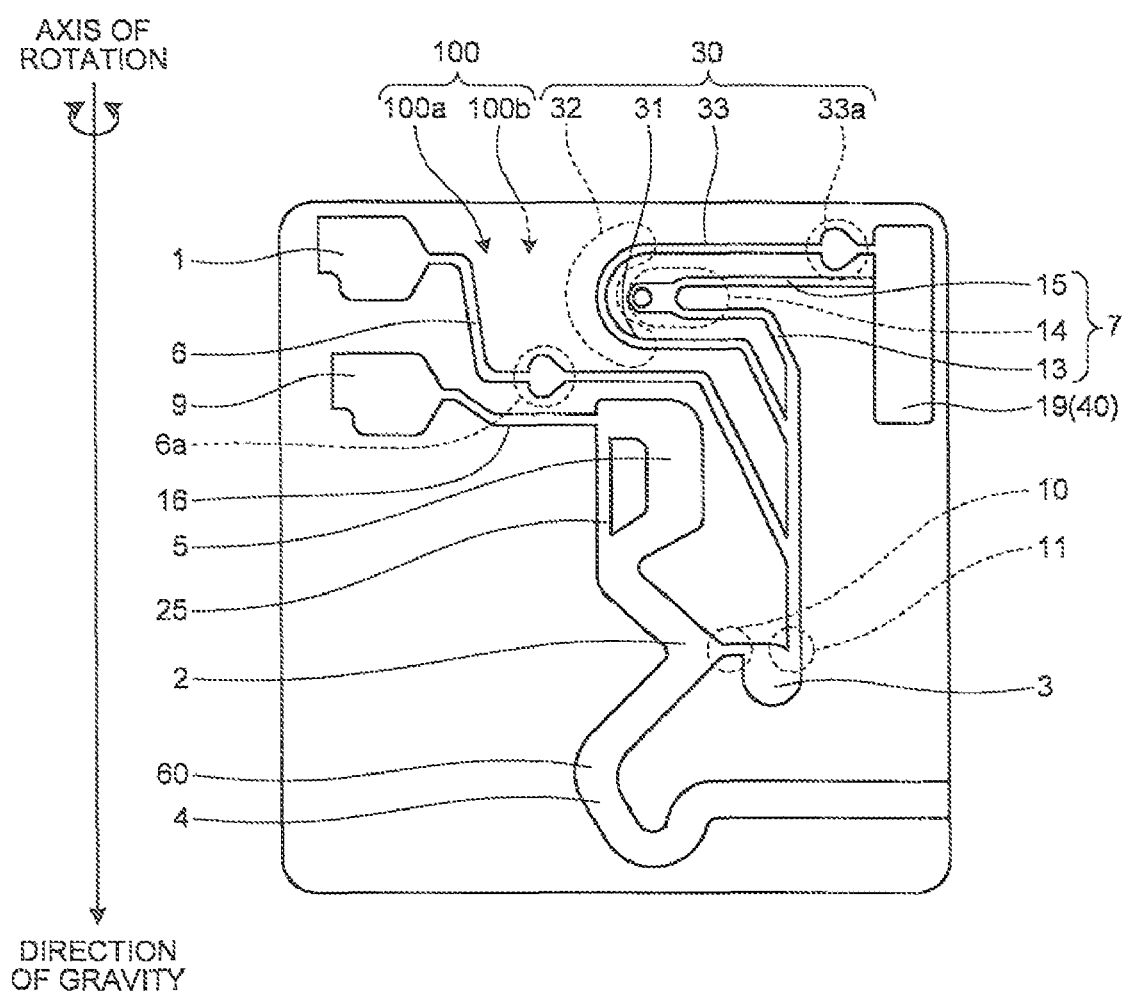
FIG. 8 is a plan view transparently illustrating another configuration example of a separation chip.

Another configuration example of the separation chip will now be described with reference to FIG. 8. FIG. 8 is a plan view transparently illustrating another separation chip configuration example.

As illustrated in FIG. 8, the separation chip according to this configuration example has main surfaces 100, more specifically, has a first main surface 100a and a second main surface 100b facing the first main surface 100a.

An integrated channel formed by the merging of one end of the suspension introduction channel 6, one end of the overflow channel 7, and one end of the insoluble component discharge channel 30 is connected to the insoluble component holding tank 3 so as to open on an upper wall face thereof on the outer circumferential side.

The insoluble component discharge channel 30 is formed from a first half portion 31 extending toward the inner circumferential side, a U-shaped folded back portion 32, and a latter half portion 33 which is folded back by the folded back portion 32 to change directions and extend toward the outer circumferential side.

The other end of the overflow channel 7 is connected so as to open onto the overflow holding tank 19, which is provided at the uppermost of and furthest toward the outer circumferential side of the separation chip.

The insoluble component discharge channel 30 is connected so as to open onto a waste tank 40, which also acts as the above-described overflow holding tank 19. The folded back portion 32 of the insoluble component discharge channel 30 is positioned further toward the inner circumferential side than the folded back portion 14 of the overflow channel 7. Further, a knob-like stop valve 33a is provided in the latter half portion 33 of the insoluble component discharge channel 30.

The other end of the suspension introduction channel 6 is connected so as to open onto the outer circumferential side of the suspension holding tank 1, which is positioned at the uppermost of and the furthest toward the inner circumferential side of the separation chip. The suspension introduction channel 6 first extends in a horizontal direction from the connecting portion with the suspension holding tank 1, then inflects and extends toward the outer circumferential direction in the direction of gravity, and again inflects and extends in a horizontal direction. A knob-like stop valve 6a is provided on that portion area. Further on from the stop valve 6a, the suspension introduction channel 6 further extends toward the outer circumferential direction in the direction of gravity so as to wrap around the upper end side of the below-described washing solution holding tank 5. Then, the suspension introduction channel 6 merges with the overflow channel 7 and the insoluble component discharge channel 30, and is connected the insoluble component holding tank 3.

The separation chip according to this configuration example has a washing solution storage tank 9. The washing solution storage tank 9 is provided on the innermost circumferential side of the separation chip, directly beneath and in parallel to the suspension holding tank 1. In this example, the washing solution storage tank 9 has approximately the same shape and size as the suspension holding tank 1.

One end of a washing solution introduction channel 16 is connected to the inner circumferential side of the washing solution storage tank 9. The washing solution introduction channel 16 is connected so as to open onto an upper portion of the washing solution holding tank 5 on the inner circumferential side, by first extending toward the outer circumferential direction in the direction of gravity, then inflecting and extending in a horizontal direction.

In this example, the washing solution holding tank 5 has a shape which is curved in an approximately reverse C shape. A gas channel 25 extending in the direction of gravity (perpendicular direction) is connected to an upper end portion of the washing solution holding tank 5 on the inner circumferential side and to a lower end portion thereof on the inner circumferential side so that these portions are in communication with each other.

The lower end portion of the washing solution holding tank 5 on the inner circumferential side is connected to an upper end of the separation liquid holding tank 2, which has a reverse C shape similar to that described above.

An inflected portion (apex on the outer circumferential side) of the separation liquid holding tank 2 is connected to an upper end portion of the insoluble component holding tank 3 on the inner circumferential side by a constricted narrow portion 10. The separation liquid discharge channel 4 is integrally connected to a lower end portion of the separation liquid holding tank 2. At an inflected portion 60 of the separation liquid discharge channel 4, the separation liquid discharge channel 4 extending toward the inner circumferential side in the direction of gravity changes direction toward the outer circumferential side in the direction of gravity. The separation liquid discharge channel 4 further extends and then inflects upwards in the outer circumferential direction to form an approximate C shape. The separation liquid discharge channel 4 then again inflects, extends in a horizontal direction, and opens onto the outside of the separation chip.

An example of operation of the above-described separation chip will now be described with reference to FIGS. 9-1, 9-2, 9-3, and 9-4.

Figures 3, 9:
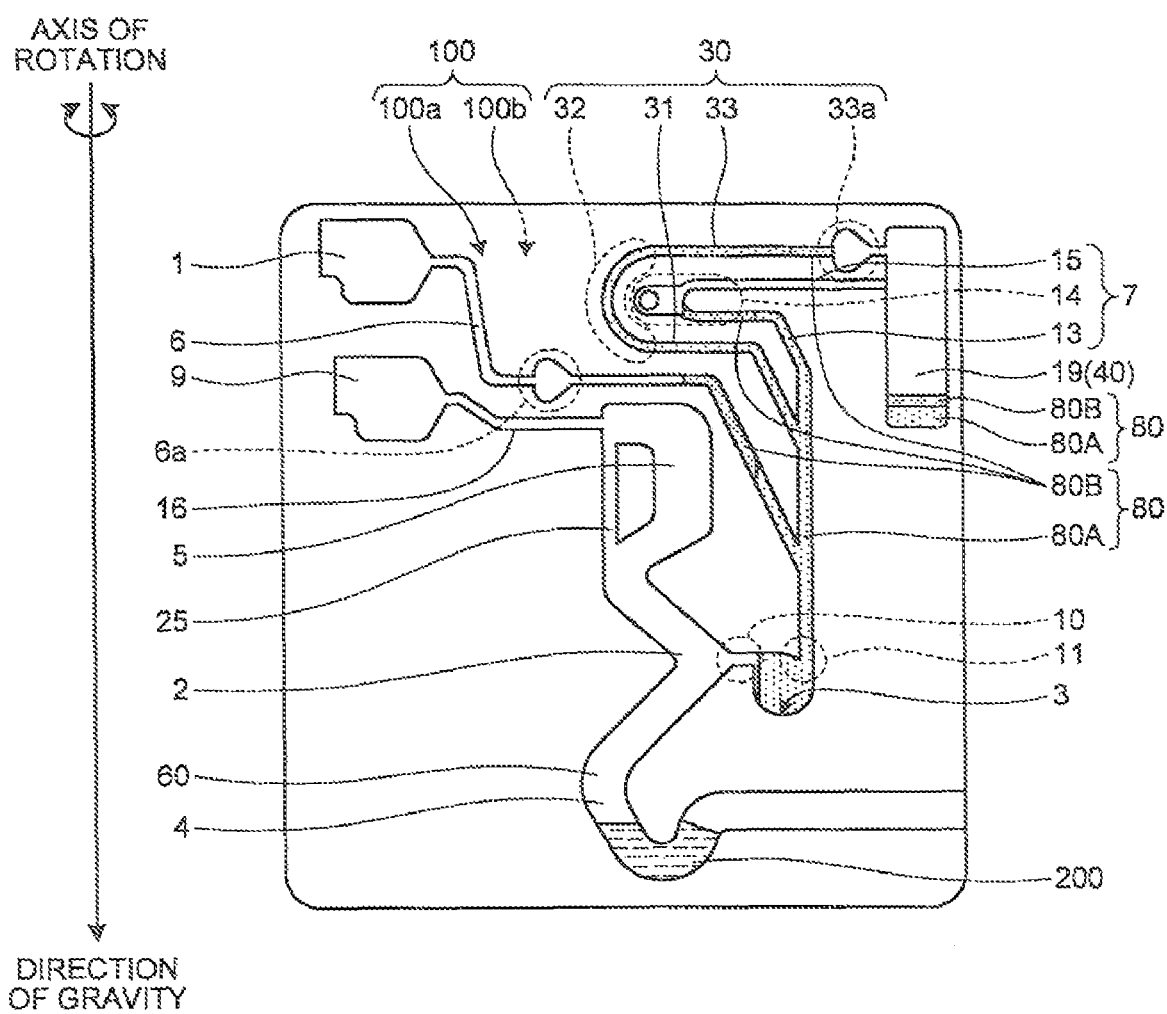
Figures 4, 9:
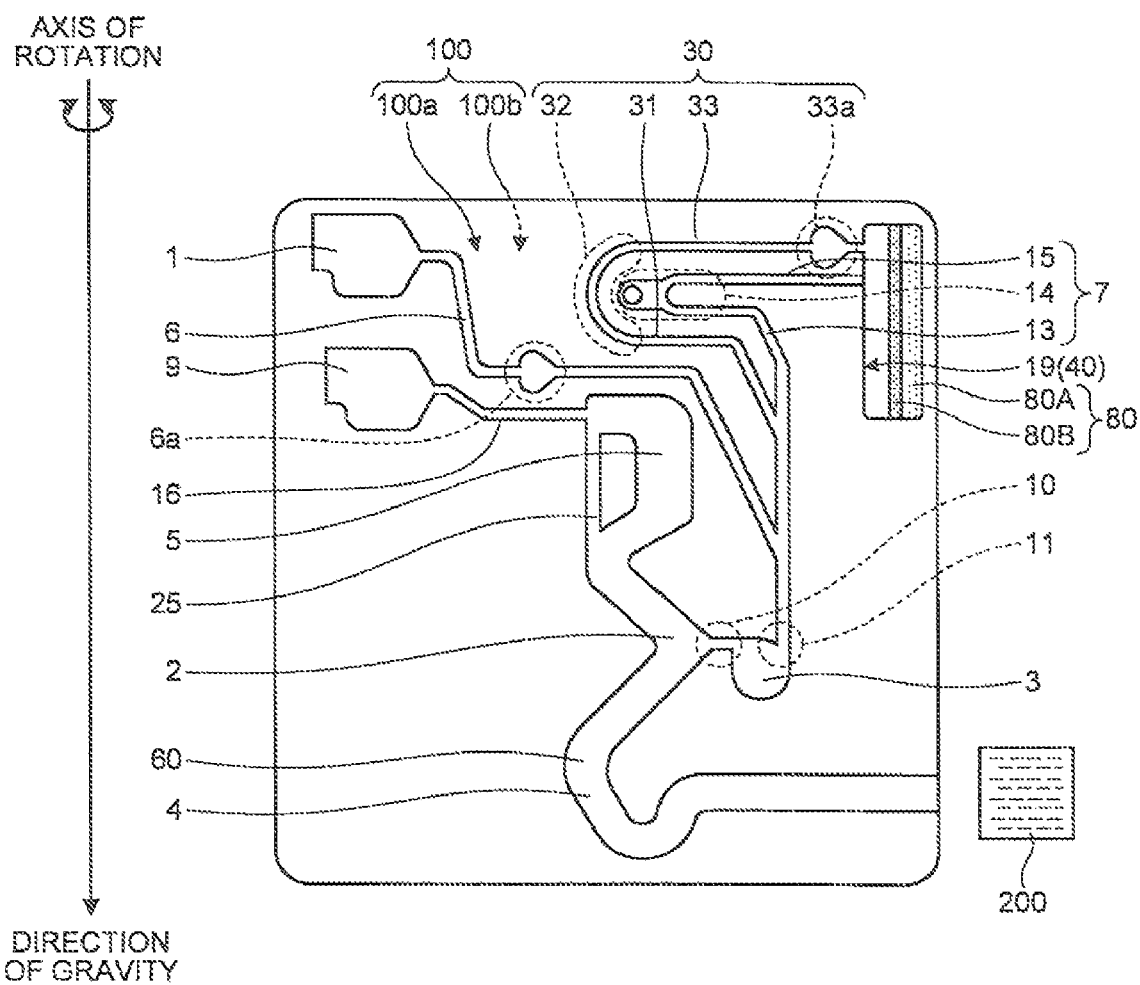

FIG. 9-1 is a schematic view (1) illustrating the operation of a separation chip. FIG. 9-2 is a schematic view (2) illustrating the operation of a separation chip. FIG. 9-3 is a schematic view (3) illustrating the operation of a separation chip. FIG. 9-4 is a schematic view (4) illustrating the operation of a separation chip.

As illustrated in FIG. 9-1, the suspension 80 is introduced into the suspension holding tank 1. Further, a washing solution is introduced into the washing solution storage tank 9, and the separation chip is mounted on a not-illustrated rotation apparatus (centrifuge). Alternatively, the suspension 80 is introduced into the suspension holding tank 1 and the washing solution is introduced into the washing solution storage tank 9 of a separation chip already mounted on a rotation apparatus.

As illustrated in FIG. 9-2, when the separation chip starts to rotate due to an initial rotation operation, the suspension 80 is fluidly fed via the suspension introduction channel 6 and introduced into the insoluble component holding tank 3. The suspension 80 is separated by the centrifugal force generated by rotation into an insoluble component 80A and a liquid component 80B. The insoluble component 80A mainly adheres to a side wall of the insoluble component holding tank 3 on the outer circumferential side. The liquid component 80B overflows from the insoluble component holding tank 3, and is introduced (fed) into the separation liquid holding tank 2 via the narrow portion 10 from the outer circumferential side. Excess suspension 80 is discharged (fed) to the overflow holding tank 19 via the overflow channel 7. At this stage, the liquid surface in the separation liquid holding tank 2, in the suspension introduction channel 6, and in the insoluble component discharge channel 30 are all defined in an approximately vertical plane of the folded back portion 14 of the overflow channel 7. Consequently, the insoluble component 80A and the liquid component 80B of the suspension 80 are separated by utilizing centrifugal force generated by rotation, and the liquid component 80B is held in the separation liquid holding tank 2. At this stage, the washing solution 90 in the washing solution storage tank 9 is held so as to adhere to the wall face of the washing solution holding tank 5 on the outer circumferential side. Then, after the insoluble component 80A and the liquid component 80B are separated, rotation is stopped.

A case will now be described in which the difference between the specific gravity of the insoluble component in the suspension and the specific gravity of the liquid component is small. When the separation chip starts to rotate due to an initial rotation operation, the suspension 80 is fluidly fed via the suspension introduction channel 6 and introduced into the insoluble component holding tank 3. The suspension 80 overflows from the insoluble component holding tank 3, and is introduced (fed) into the separation liquid holding tank 2 via the narrow portion 10 from the outer circumferential side. Excess suspension 80 is discharged (fed) to the overflow holding tank 19 via the overflow channel 7. At this stage, the liquid surface in the separation liquid holding tank 2, in the suspension introduction channel 6, and in the insoluble component discharge channel 30 are all defined in an approximately vertical plane of the folded back portion 14 of the overflow channel 7. The suspension 80 is progressively separated by the centrifugal force generated by rotation into an insoluble component 80A and a liquid component 80B. The insoluble component 80A mainly adheres to a side wall of the insoluble component holding tank 3 on the outer circumferential side. The liquid component 80B is mainly held in the separation liquid holding tank 2. Then, after separating the insoluble component 80A and the liquid component 80B of the suspension 80 by utilizing centrifugal force generated by rotation, rotation is stopped.

As illustrated in FIG. 9-3, when rotation of the separation chip is stopped, the suspension 80 falls down in the separation liquid discharge channel 4 due to the action of gravity, and moves toward the outer circumferential side of the separation liquid discharge channel 4 to below the inflected portion 60, where it accumulates. At this stage, the washing solution 90 falls from the washing solution holding tank 5 positioned above the separation liquid holding tank 2. Consequently, the washing solution 90 promotes the falling down of the liquid component 80B due to gravity while simultaneously cleaning the inside of the separation liquid holding tank 2 and the inside of the separation liquid discharge channel 4. Further, the washing solution 90 also accumulates in the separation liquid discharge channel 4, where it produces a mixture 200 with the liquid component 80B. As a result of using the washing solution 90, the recovery ratio of the liquid component 80B is increased. Moreover, the recovery ratio of the liquid component 80B can even be stabilized.

The separation liquid discharge channel 4 has a section midway along the channel which has a smaller channel cross-sectional area than the channel cross-sectional area at the connecting portion with the separation liquid holding tank 2. This cross-sectional area becomes gradually smaller. Consequently, capillary force can be used in addition to gravity, so that the liquid component 80B is made to fall in a shorter time. Further, the separation liquid discharge channel 4 is inflected toward the outer circumferential side midway along the channel, and has a section extending toward the outer circumferential side in the direction of gravity. The liquid component 80B accumulates at a section extending to the outer circumferential side in the direction of gravity in the separation liquid discharge channel.

At this stage, the suspension 80 containing a large amount of insoluble component 80A proceeds through the insoluble component discharge channel 30 by capillarity. This suspension 80 then passes through, in order, from the first half portion 31, the folded back portion 32, and the latter half portion 33 of the insoluble component discharge channel 30, and proceeds as far as the stop valve 33a to fill the insoluble component discharge channel 30. Subsequently, the separation chip is again rotated.

As illustrated in FIG. 9-4, the mixture 200 accumulated in the separation liquid discharge channel 4 is completely discharged out of the separation chip due to the centrifugal force generated by further rotation.

At this stage, the suspension containing a large amount of insoluble component 80A in the insoluble component holding tank 3, in the overflow channel 7, in the suspension introduction channel 6, and in the insoluble component discharge channel 30 (the suspension having an increased ratio of insoluble component 80A) passes through the insoluble component discharge channel 30, and due to a siphon effect is completely discharged (fed) to the overflow holding tank 19 also acting as the waste tank 40.

The size of the optionally-provided vent hole in the separation chip is generally in the range of 0.1 mm to 5.0 mm, and may preferably be in the range of 0.5 mm to 2.0 mm. Further, the vent hole may be replaced with a tubular vent channel. In the case of a vent channel, the position and the angle are not especially limited. However, to prevent a specimen or a reagent from flowing in during feeding, it is preferred that the vent channel extends towards and is open to the axis of rotation direction (inner circumferential side) from the respective storage tanks.

It is preferred that the inner wall face of at least some of the tanks and channels of the separation chip has been subjected to an adsorption suppression treatment. If the inner wall faces of the separation chip have been subjected to an adsorption suppression treatment, errors in measurement, analysis, and reaction caused by reduction in the component concentration due to adsorption of the suspension can be reduced, so that accuracy can be improved. Furthermore, the fed liquid may stagnate if the suspension introduced into the tanks is adsorbed on the inner walls of the separation chip. However, by carrying out an adsorption suppression treatment, this problem can be resolved. Examples of methods for the adsorption suppression treatment which may be used include a coating treatment in which a hydrophilic polymer material is adsorbed on a surface by static electricity, and a method in which a hydrophilic polymer material is covalently bonded to the surface of the resin and tightly fixed by irradiating a high-energy beam.

The material of the separation chip is not especially limited. Examples thereof may include a resin, glass and the like. In particular, from the perspective of facilitating observation of the tanks and channels externally from the separation chip, at least a part of the tanks and channels may be transparent or opaque. If the tanks and the channels of the separation chip are transparent, the liquid feeding condition can be easily observed externally from the separation chip.

As a transparent material for forming the separation chip, various organic and inorganic materials may be used. Preferably used examples include a resin such as poly(methyl methacrylate) (PMMA), polycarbonate, polypropylene, polyethylene, polymethylpentene, polystyrene, polytetrafluoroethylene, ABS resin, polydimethylsiloxane, and silicone and the like, as well as copolymers or complexes including such a polymer compound; a glass such as quartz glass, Pyrex(registered trade mark) glass, soda glass, borate glass, silicate glass, borosilicate glass and the like, and complexes thereof; a metal having a surface coated with an insulating material and complexes thereof; and a ceramic and complexes thereof and the like. Among these, it is especially preferred to use poly(methyl methacrylate) (PMMA), polycarbonate, polystyrene, polytetrafluoroethylene, and polypropylene.

Further, as a chemically stable material which has chemical resistance and water resistance, various organic or inorganic materials may be used. Preferably used examples include a resin such as polypropylene, polyethylene, polymethylpentene, polystyrene, polytetrafluoroethylene, polydimethylsiloxane, and silicone and the like, as well as copolymers or complexes including a polymer compound of such a resin; a glass such as quartz glass, Pyrex (registered trade mark) glass, soda glass, borate glass, silicate glass, borosilicate glass and the like, and complexes thereof; and a ceramic and complexes thereof and the like. Among these, it is especially preferred to use polypropylene, polyethylene, polymethylpentene, and polystyrene.

The method for manufacturing the separation chip is not especially limited. For example, the separation chip may be manufactured by joining a plate-like substrate having concave portions for the respective tanks and channels formed thereon to another substrate or a film. Alternatively, the separation chip may be manufactured by sandwiching a substrate having channel-forming slits on either side with two substrates. If the material is a resin, the concave portions for the respective tanks and channels may be formed by a typical molding method which uses a mold. Examples of such methods include injection molding, press molding, blow molding, vacuum molding, hot embossing and the like.

The separation chip may be used for the separation of an insoluble component and a liquid component from a suspension. For example, if a suspension is introduced into a suspension liquid holding tank of the separation chip, and then the separation chip is rotated by a rotor or the like, the suspension in the separation chip is fed from the suspension liquid holding tank to an insoluble component holding tank. The insoluble component is held in the insoluble component holding tank, and the separation liquid is fed to a separation liquid holding tank. Subsequently, by stopping rotation, the insoluble component can be obtained. The rotation speed and rotation time of the separation chip depend on the type and the amount of the suspension. However, for example, when separating blood cells from blood, the rotation speed is generally 10 G to 6000 G, and the rotation time is generally 1 minute to 10 minutes. Preferably, the rotation speed is 1000 G to 4000 G, and the rotation time is 1 minute to 5 minutes.

EXAMPLES

Comparative Example 1

Plasma separation from human blood was performed using a separation chip having the configuration already described with reference to FIGS. 1-1 and 1-2. This separation chip has a suspension holding tank capacity of 300 μL, and an insoluble component holding tank capacity of 90 μL. A separation liquid holding tank forms a channel integrally with a separation liquid discharge channel. The suspension holding tank is connected with the separation liquid holding tank. The separation liquid holding tank is connected with the insoluble component holding tank by a narrow portion. The cross-sectional area of the narrow portion is 2.1 mm$^2$.

Using 7 separation chips, 150 μL, of human blood collected from 7 people with an EDTA blood collection tube was charged into the suspension holding tanks, and the upper face of the separation chips was sealed. The separation chips were mounted on a horizontal rotor so that the suspension holding tanks were positioned on the inner circumferential side, and then rotated for 2 minutes at a rotation speed which applied a centrifugal force of 2000 G. FIG. 1-1 illustrates a mode as viewed from obliquely above of a state in which a separation chip is arranged on a horizontal rotor. After rotation was stopped, gas bubbles had entered the insoluble component holding tank for 3 of the 7 specimens. In one of these specimens, the blood cell component had overflowed as far as the separation liquid holding tank. The amount of plasma obtained from the separation liquid discharge channel is shown in Table 1.

TABLE 1

|  | CHIP 1 | CHIP 2 | CHIP 3 | CHIP 4 | CHIP 5 | CHIP 6 | CHIP 7 |
| --- | --- | --- | --- | --- | --- | --- | --- |
| PLASMA AMOUNT (μl) (FINDING) | 64.8 (GAS BUBBLES) | 53.8 | 71.1 (GAS BUBBLES) | 55.4 | 56.6 | >90 (BLOOD CELLS COULD NOT BE SEPARATED) | 56.4 |

The amount of plasma in the 6 specimens for which plasma could be obtained in the separation liquid discharge channel was uneven, ranging from 53.8 μL to 71.1 μL. The effect of gas bubbles remaining in the insoluble component holding tank was confirmed.

Comparative Example 2

Plasma separation from human blood was performed using a separation chip having the configuration already described with reference to FIG. 2. This separation chip has a suspension holding tank capacity of 400 μL, and an insoluble component holding tank capacity of 90 μL. A separation liquid holding tank forms a channel integrally with a separation liquid discharge channel. The suspension holding tank is connected with the separation liquid holding tank. The separation liquid holding tank is connected with the insoluble component holding tank by a narrow portion. The cross-sectional area of the narrow portion is 2.1 mm².

Using 7 chips, 150 μL of human blood collected from 7 people with an EDTA blood collection tube was charged into the suspension holding tanks. The separation chips were mounted on an angle rotor so that the suspension holding tanks were positioned on the inner circumferential side, and then rotated for 2 minutes at a rotation speed which applied a centrifugal force of 2000 G. FIG. 2 illustrates an embodiment as viewed from a horizontal plane of a state in which a separation chip is arranged on an angle rotor. After rotation was stopped, gas bubbles had entered the insoluble component holding tank for 2 of the 7 specimens. In one of these specimens, the blood cell component was mixed with the separation liquid.

Example 1

Plasma separation from human blood was performed using a separation chip having the configuration already described with reference to FIGS. 3-1 and 3-2. This separation chip has a suspension holding tank capacity of 300 μL, and an insoluble component holding tank capacity of 90 μL. A separation liquid holding tank forms a channel integrally with a separation liquid discharge channel. The suspension holding tank is connected with the insoluble component holding tank. The separation liquid holding tank is connected with the cell component and the plasma were separated. The amount of plasma obtained from the separation liquid discharge channel is shown in Table 2.

TABLE 2

| | CHIP 1 | CHIP 2 | CHIP 3 | CHIP 4 | CHIP 5 | CHIP 6 | CHIP 7 |
|---|---|---|---|---|---|---|---|
| PLASMA AMOUNT (μl) | 52.8 | 53.5 | 56.1 | 55.8 | 56.7 | 56.3 | 54.5 |

The amount of plasma in the 7 specimens for which plasma could be obtained in the separation liquid discharge channel stayed within the range of 52.8 μL to 56.7 μL.

Example 2

Plasma separation from human blood was performed using a separation chip having the configuration already described with reference to FIG. 4. This separation chip has a suspension holding tank capacity of 300 μL, and an insoluble component holding tank capacity of 90 μL. A separation liquid holding tank forms a channel integrally with a separation liquid discharge channel. The suspension holding tank is connected with the insoluble component holding tank. The separation liquid holding tank is connected with the insoluble component holding tank by a narrow portion. The cross-sectional area of the narrow portion is 2.1 cm².

Using 7 separation chips, 150 μL of human blood collected from 7 people with an EDTA blood collection tube was charged into the suspension holding tanks. The separation chips were placed in tubes, which were then mounted on an angle rotor so that the suspension holding tanks were positioned on the inner circumferential side. The separation chips were rotated for 2 minutes at a rotation speed which applied a centrifugal force of 2000 G. FIG. 4 illustrates an embodiment as viewed from a horizontal plane of a state in which a separation chip is arranged on an angle rotor. After rotation was stopped, among the 7 specimens, no chips were observed in which gas bubbles had entered the insoluble component holding tank. In all of the 7 specimens, the blood cell component and the plasma were separated. The amount of plasma obtained from the separation liquid discharge channel is shown in Table 3.

insoluble component holding tank by a narrow portion. The cross-sectional area of the narrow portion is 2.1 mm².

Using 7 separation chips, 150 μL of human blood collected from 7 people with an EDTA blood collection tube was charged into the suspension holding tanks, and the upper face of the separation chips was sealed. The separation chips were mounted on a horizontal rotor so that the suspension holding tanks were positioned on the inner circumferential side, and then rotated for 2 minutes at a rotation speed which applied a centrifugal force of 2000 G. FIG. 3-1 illustrates an embodiment as viewed from obliquely above of a state in which a separation chip is arranged on a horizontal rotor. After rotation was stopped, among the 7 specimens, no chips were observed in which gas bubbles had entered the insoluble component holding tank. In all of the 7 specimens, the blood

TABLE 3

| | CHIP 1 | CHIP 2 | CHIP 3 | CHIP 4 | CHIP 5 | CHIP 6 | CHIP 7 |
|---|---|---|---|---|---|---|---|
| PLASMA AMOUNT (μl) | 54.5 | 54.6 | 57.1 | 56.6 | 53.9 | 58.0 | 57.3 |

The obtained plasma amounts stayed within the range of 53.9 μL to 58 μL.

Example 3

Plasma was separated from whole blood using separation chips having the configuration already described with reference to FIG. 4 by applying a centrifugal force of 1000 G, 2000 G, and 3000 G. The components of the whole blood and the plasma were analyzed using the multi-analysis automated hematology analyzer K-1000 manufactured by Sysmex Corporation under the same conditions as in the above-described Example 2, except for changing the centrifugal force and using one type of specimen. The analysis results for the whole blood are shown in Table 4, and the analysis results for the plasma are shown in Table 5. The blood cell component could be sufficiently removed by centrifugal separation at 2000 G for 1 minute.

TABLE 4

(WHOLE BLOOD COMPONENT)

| | | |
|---|---|---|
| WHOLE BLOOD COMPONENT ANALYSIS | WBC (WHITE BLOOD CELLS) [× 100/µl] | 48 |
| | RBC (RED BLOOD CELLS) [× 10000/µl] | 440 |
| | HGB (HEMOGLOBIN) [g/dl] | 13.1 |
| | HCT (HEMOTACRIT) [%] | 38.5 |
| | PLT (PLATELETS) [× 10000/µl] | 21.2 |

TABLE 5

(PLASMA COMPONENT)

| | | 1 MINUTE | 2 MINUTES | 3 MINUTES | 4 MINUTES | 5 MINUTES |
|---|---|---|---|---|---|---|
| PLASMA COMPONENT ANALYSIS AFTER 3,000 G CENTRIFUGAL SEPARATION | WBC (WHITE BLOOD CELLS) [×100/µl] | 0 | 0 | 0 | 0 | 0 |
| | RBC (RED BLOOD CELLS) [×10000/µl] | 1 | 0 | 0 | 0 | 0 |
| | HGB (HEMOGLOBIN) [g/dl] | 0 | 0 | 0 | 0 | 0 |
| | HCT (HEMOTACRIT) [%] | 0 | 0 | 0 | 0 | 0 |
| | PLT (PLATELETS) [×10000/µl] | 0 | 0 | 0 | 0 | 0 |
| PLASMA COMPONENT ANALYSIS AFTER 2,000 G CENTRIFUGAL SEPARATION | WBC (WHITE BLOOD CELLS) [×100/µl] | 0 | 0 | 0 | 0 | 0 |
| | RBC (RED BLOOD CELLS) [×10000/µl] | 2 | 0 | 0 | 0 | 0 |
| | HGB (HEMOGLOBIN) [g/dl] | 0.1 | 0.1 | 0.1 | 0 | 0 |
| | HCT (HEMOTACRIT) [%] | 0.2 | 0 | 0 | 0 | 0 |
| | PLT (PLATELETS) [×10000/µl] | 0.5 | 0 | 0 | 0 | 0 |
| PLASMA COMPONENT ANALYSIS AFTER 1,000 G CENTRIFUGAL SEPARATION | WBC (WHITE BLOOD CELLS) [×100/µl] | 0 | 1 | 0 | 0 | 0 |
| | RBC (RED BLOOD CELLS) [×10000/µl] | 0 | 0 | 0 | 0 | 0 |
| | HGB (HEMOGLOBIN) [g/µl] | 0.1 | 0.1 | 0 | 0 | 0 |
| | HCT (HEMOTACRIT) [%] | 0 | 0 | 0 | 0 | 0 |
| | PLT (PLATELETS) [×10000/µl] | 7 | 1.4 | 0.2 | 0.1 | 0 |

Example 4

Plasma separation from human blood was performed using a separation chip having the configuration already described with reference to FIG. 5. The separation chip used in the present example has a suspension holding tank capacity of 200 µL, and an insoluble component holding tank capacity of 93 µL. A separation liquid holding tank forms a channel integrally with a separation liquid discharge channel. The suspension holding tank is connected with the insoluble component holding tank. The separation liquid holding tank is connected with the insoluble component holding tank by a narrow portion. The cross-sectional area of the narrow portion is 2.1 square millimeters (mm²). The cross-sectional area of a first half portion of an overflow channel is 0.03 mm². Further, although the separation chip used in the present example has a washing solution storage tank, washing solution was not charged therein.

Using 7 separation chips, from 160 µL to 200 µL of human blood collected from 7 people with an EDTA blood collection tube was charged into the suspension holding tanks. The separation chips were placed in tubes, which were then mounted on a horizontal rotor so that the suspension holding tanks were positioned on the inner circumferential side. The separation chips were rotated for 2 minutes at a rotation speed which applied a centrifugal force of 2000 G. FIG. 5 illustrates an embodiment as viewed from a horizontal plane of a state in which a separation chip is arranged on an angle rotor. The separation chips used in the present example are designed so that when the separation chips are rotated at 2000 G, the separation liquid holding tank and the insoluble component holding tank would hold a combined solution total of 133 µL during rotation due to the function of the overflow channel. After rotation was stopped, among the 7 specimens, no chips were observed in which gas bubbles had entered the insoluble component holding tank. In all of the 7 specimens, the blood cell component and the plasma were separated. Excess whole blood was discharged via the overflow channel. Checking of the amount of obtained plasma showed that, despite the charged amount of whole blood being different, there was little unevenness in the obtained amount of plasma. Therefore, a quantitative performance was secured by providing the overflow channel. The amount of plasma obtained from the separation liquid discharge channel is shown in Table 6.

TABLE 6

|  | CHIP 1 | CHIP 2 | CHIP 3 | CHIP 4 | CHIP 5 | CHIP 6 | CHIP 7 |
| --- | --- | --- | --- | --- | --- | --- | --- |
| PLASMA AMOUNT (μl) | 38.5 | 37.5 | 38.9 | 38.4 | 38.4 | 39 | 38.5 |

Example 5

Plasma separation from human blood was performed using a separation chip having the configuration already described with reference to FIG. 5. The separation chip used in the present example has a suspension holding tank capacity of 200 μL, and an insoluble component holding tank capacity of 93 μL. A separation liquid holding tank forms a channel integrally with a separation liquid discharge channel. The suspension holding tank is connected with the insoluble component holding tank. The separation liquid holding tank is connected with the insoluble component holding tank by a narrow portion. The cross-sectional area of the narrow portion is 2.1 mm². The cross-sectional area of a first half portion of an overflow channel is 0.03 mm².

The separation chip illustrated in FIG. 5 differs from the separation chips illustrated in FIGS. 3 and 4 in having a washing solution holding tank, a washing solution storage tank, and an overflow channel. 40 μL of a 1% glycerol solution was charged into the washing solution storage tank as a washing solution.

Using 7 separation chips, 160 to 200 μL of human blood collected from 7 people with an EDTA blood collection tube was charged into the suspension holding tanks. The separation chips were placed in tubes, which were then mounted on a horizontal rotor so that the suspension holding tanks were positioned on the inner circumferential side. The separation chips were rotated for 2 minutes at a rotation speed which applied a centrifugal force of 2000 G. FIG. 5 illustrates an embodiment as viewed from a horizontal plane of a state in which a separation chip is arranged on an angle rotor. The separation chips used in the present example are designed so that when the separation chips are rotated at 2000 G, the separation liquid holding tank and the insoluble component holding tank would hold a combined solution total of 133 μL during rotation due to the function of the overflow channel. After rotation was stopped, among the 7 specimens, no chips were observed in which gas bubbles had entered the insoluble component holding tank. In all of the specimens, the blood cell component and the plasma were separated. Further, the separation liquid holding tank and the separation liquid discharge channel had been washed by the washing solution. Excess whole blood was discharged via the overflow channel. The total amount of the obtained plasma and washing solution were checked. The results are shown in Table 7.

TABLE 7

|  | CHIP 1 | CHIP 2 | CHIP 3 | CHIP 4 | CHIP 5 | CHIP 6 | CHIP 7 |
| --- | --- | --- | --- | --- | --- | --- | --- |
| TOTAL AMOUNT | 73.3 | 76.1 | 76.3 | 77.5 | 75.9 | 78.1 | 77.3 |

As shown in Table 7, the amount of obtained plasma and washing solution stayed within the range of 73.3 μL to 78.1 μL. Despite the charged amount of whole blood being different, there was little unevenness in the amount of the obtained mixture of plasma and washing solution. Therefore, a quantitative performance was secured by providing the overflow channel. Further, differences in the recovered amounts were reduced due to the use of a washing solution.

Example 6

Plasma separation from human blood was performed using a separation chip having the configuration already described with reference to FIGS. 6-1, 6-2, 6-3, and 6-4. The separation chip used in the present example has a suspension holding tank capacity of 1 mL, and an insoluble component holding tank capacity of 500 μL. The volume of separation liquid held in a separation liquid holding tank is regulated by the position of a folded back portion of the overflow channel to be 200 μL. The separation liquid holding tank forms a channel integrally with a separation liquid discharge channel. The suspension holding tank is connected with the insoluble component holding tank. The separation liquid holding tank is connected with the insoluble component holding tank by a narrow portion. The cross-sectional area of the narrow portion is 3 mm².

The separation chip illustrated in FIG. 6-1 differs from the separation chip illustrated in FIG. 5 in not having a washing solution holding tank and a washing solution storage tank, and in having an insoluble component discharge channel. Further, as described with reference to FIG. 6-4, a separation liquid recovery container 300 for separation liquid recovery can be mounted on a first protrusion 50B, which includes a separation liquid discharge channel 4. Consequently, the separation liquid can be recovered in a container and used as is for analysis and measurement without requiring any operations by a person or equipment therefor.

Plasma separation from human blood was performed using a separation chip having the configuration already described with reference to FIGS. 6-1, 6-2, and 6-3. 800 μL of human blood was charged into the suspension holding tank 1. A 2 mL tube for plasma recovery was mounted at the location where the separation liquid discharge channel 4 was provided, and the separation chip was mounted on a centrifuge (rotation apparatus). The separation chip was rotated for 2 minutes at a rotation speed at which the centrifugal force at the narrow section 10 would be 2000 G. Then, rotation was stopped and the separation chip was left to stand for 30 seconds. The separation chip was again rotated at the same rotation speed for 30 seconds, and then rotation was stopped. Consequently, it was confirmed that, as designed, about 200 μL of plasma was recovered in the 2 mL tube, and that the blood cell component was removed. Further, the suspension containing a large amount of insoluble component in the insoluble component holding tank 3, in the suspension introduction channel 6, and in the overflow channel 7 was discharged to the overflow holding tank 19.

Example 7

Plasma separation from human blood was performed using a separation chip having the configuration already described with reference to FIG. 8. The separation chip used in the present example has a suspension holding tank capacity of 250 μL, and an insoluble component holding tank capacity of 55 μL. The volume of the separation liquid holding tank is regulated by the position of a folded back portion of the overflow channel to be 26 μL. The separation liquid holding tank forms a channel integrally with a separation liquid discharge channel. The suspension holding tank is connected with the insoluble component holding tank. The separation liquid holding tank is connected with the insoluble component holding tank by a narrow portion. The cross-sectional area of the narrow portion is 3 mm$^2$.

The separation chip illustrated in FIG. 8 differs from the separation chip illustrated in FIG. 6-1 in having a washing solution holding tank and a washing solution storage tank.

Plasma separation from human blood was performed using a separation chip having the configuration already described with reference to FIG. 8. 150 μL of human blood was charged into the suspension holding tank 1. 80 μL of washing solution was charged into the washing solution storage tank 9, and the separation chip was mounted on a centrifuge (rotation apparatus). The separation chip was rotated for 2 minutes at a rotation speed at which the centrifugal force at the narrow section 10 would be 1500 G. Then, rotation was stopped and the separation chip was left to stand for 30 seconds. The separation chip was again rotated at the same rotation speed for 30 seconds, and then rotation was stopped. Consequently, it was confirmed that, as designed, about 26 μL of plasma was recovered externally from the separation chip, and that the blood cell component was removed. Further, the suspension containing a large amount of insoluble component in the insoluble component holding tank 3, in the suspension introduction channel 6, and in the overflow channel 7 was discharged to the overflow holding tank 19 (waste tank 40).

Industrial Applicability

The separation chip can be preferably used for performing various measurements and tests by separating a suspension such as blood, for example, into an insoluble component and a liquid component.

The invention claimed is:

1. A separation chip for separating an insoluble component from a suspension using centrifugal force produced by rotation comprising:
   a suspension holding tank, a separation liquid holding tank, and an insoluble component holding tank arranged in order from an inner circumferential side during rotation,
   wherein the suspension holding tank and the insoluble component holding tank are connected to each other,
   the insoluble component holding tank and the separation liquid holding tank are connected to each other by a narrow portion, and
   in the insoluble component holding tank, a connecting portion with the suspension holding tank is positioned further toward an outer circumferential side than the narrow portion.

2. The separation chip according to claim 1, wherein the suspension holding tank and the insoluble component holding tank arc connected to each other by a suspension introduction channel, and an opening of the suspension introduction channel in the insoluble component holding tank is positioned further toward an outer circumferential side than the narrow portion, and
   the separation liquid holding tank can hold a liquid component which has passed through the narrow portion.

3. The separation chip according to claim 2, further comprising an overflow channel having one end connected to the suspension introduction channel and the insoluble component holding tank, and wherein the overflow channel has a folded back portion which first extends toward the inner circumferential side from a connecting portion with the suspension introduction channel or the insoluble component holding tank, then changes direction and extends toward the outer circumferential side.

4. The separation chip according to claim 3, wherein the folded back portion of the overflow channel further comprises a vent hole communicating outwardly of the separation chip.

5. The separation chip according to claim 3, further comprising an insoluble component discharge channel connected to one or more selected from the group consisting of the insoluble component holding tank, the suspension introduction channel, and the overflow channel.

6. The separation chip according to claim 5, wherein the insoluble component discharge channel first extends toward the inner circumferential side from a connecting portion with the insoluble component holding tank, and then folds back toward the outer circumferential side at the inner circumferential side further than the folded back portion of the overflow channel.

7. The separation chip according to claim 6, wherein the folded back portion of the insoluble component discharge channel is positioned above the narrow portion.

8. The separation chip according to claim 1, wherein the connecting portion between the insoluble component holding tank and the suspension holding tank is positioned on a wall face of the insoluble component holding tank on the outer circumferential side.

9. The separation chip according to claim 1, further comprising a separation liquid discharge channel which is connected to the separation liquid holding tank, extends in the direction of gravity, and discharges the liquid component from the separation liquid holding tank.

10. The separation chip according to claim 9, wherein the separation liquid discharge channel extends toward the outer circumferential side and the direction of gravity.

11. The separation chip according to claim 9, wherein the separation liquid discharge channel has a section midway along the channel having a smaller channel cross-sectional area than a channel cross-sectional area at a connecting portion with the separation liquid holding tank.

12. The separation chip according to claim 1, wherein the narrow portion is positioned above the insoluble component holding tank.

13. The separation chip according to claim 1, further comprising a washing solution holding tank positioned above the separation liquid holding tank, connects to the separation liquid holding tank, and can hold a washing solution during rotation.

14. A method for separating an insoluble component from a suspension with the separation chip according to claim 1, comprising:
   separating and holding the insoluble component using centrifugal force by rotating the separation chip, in which a suspension is introduced into the suspension holding tank, around an axis of rotation to dispense the suspension to the insoluble component holding tank;

holding in the separation liquid holding tank the liquid component separated by the centrifugal force and which passes through the narrow portion connecting the insoluble component holding tank and the separation liquid holding tank; and discharging the liquid component held in the separation liquid holding tank from the separation liquid holding tank by stopping rotation of the separation chip.

15. The separation method according to claim 14, wherein the suspension is blood.

* * * * *